(12) United States Patent
Fincke et al.

(10) Patent No.: US 7,576,296 B2
(45) Date of Patent: *Aug. 18, 2009

(54) THERMAL SYNTHESIS APPARATUS

(75) Inventors: James R. Fincke, Idaho Falls, ID (US);
Brent A. Detering, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 824 days.

This patent is subject to a terminal disclaimer.

(21) Appl. No.: 10/843,965

(22) Filed: May 11, 2004

(65) Prior Publication Data

US 2004/0208805 A1    Oct. 21, 2004

Related U.S. Application Data

(60) Division of application No. 09/781,931, filed on Feb. 12, 2001, now Pat. No. 6,821,500, application No. 10/843,965, which is a continuation-in-part of application No. 09/320,784, filed on May 27, 1999, now Pat. No. 6,187,226, which is a continuation-in-part of application No. 09/076,922, filed on May 12, 1998, now Pat. No. 5,935,293, which is a continuation-in-part of application No. 08/404,395, filed on Mar. 14, 1995, now Pat. No. 5,749,937.

(60) Provisional application No. 60/181,488, filed on Feb. 10, 2000.

(51) Int. Cl.
*B23K 10/00* (2006.01)
(52) U.S. Cl. .............................. 219/121.36; 219/121.51; 219/75; 75/10.19
(58) Field of Classification Search ............ 219/121.51, 219/121.5, 121.36, 121.37, 121.38, 121.59, 219/121.43, 75, 74; 423/335; 75/10.19, 75/10.21, 10.28, 3.46, 346
See application file for complete search history.

(56) References Cited

U.S. PATENT DOCUMENTS 2,475,282 A    7/1949    Hasche (Continued)

FOREIGN PATENT DOCUMENTS

DE    1142159    7/1960

(Continued)

OTHER PUBLICATIONS

Down, M. G., "Titanium Production by a Plasma Process". Final Technical Report, Materials Laboratory, Air Force Wright Aeronautical Laboratories (#AD A 121892) May 1982, pp. 1-8.

(Continued)

*Primary Examiner*—Mark H Paschall
(74) *Attorney, Agent, or Firm*—Trask Britt

(57) ABSTRACT

An apparatus for thermal conversion of one or more reactants to desired end products includes an insulated reactor chamber having a high temperature heater such as a plasma torch at its inlet end and, optionally, a restrictive convergent-divergent nozzle at its outlet end. In a thermal conversion method, reactants are injected upstream from the reactor chamber and thoroughly mixed with the plasma stream before entering the reactor chamber. The reactor chamber has a reaction zone that is maintained at a substantially uniform temperature. The resulting heated gaseous stream is then rapidly cooled by passage through the nozzle, which "freezes" the desired end product(s) in the heated equilibrium reaction stage, or is discharged through an outlet pipe without the convergent-divergent nozzle. The desired end products are then separated from the gaseous stream.

18 Claims, 11 Drawing Sheets

U.S. PATENT DOCUMENTS

| | | |
|---|---|---|
| 2,552,308 A | 5/1951 | Buchmann et al. |
| 2,686,195 A | 8/1954 | McAdams et al. |
| 3,051,639 A | 8/1962 | Anderson |
| 3,123,464 A | 3/1964 | Casey et al. |
| 3,211,548 A | 10/1965 | Scheller et al. |
| 3,408,164 A | 10/1968 | Johnson |
| 3,429,691 A | 2/1969 | McLaughlin |
| 3,630,718 A | 12/1971 | Neuenschwander |
| 3,668,108 A | 6/1972 | Houseman |
| 3,682,142 A | 8/1972 | Newkirk |
| 3,738,824 A | 6/1973 | Davis et al. |
| 3,840,750 A | 10/1974 | Davis et al. |
| 3,848,068 A | 11/1974 | Rice |
| 3,891,562 A | 6/1975 | Mogensen et al. |
| 3,899,573 A | 8/1975 | Shaw et al. |
| 3,914,573 A | 10/1975 | Muehlberger |
| 3,954,954 A | 5/1976 | Davis et al. |
| 3,976,442 A | 8/1976 | Paull et al. |
| 3,989,512 A | 11/1976 | Sayce |
| 3,992,193 A | 11/1976 | Fey et al. |
| 4,022,872 A | 5/1977 | Carson et al. |
| 4,080,194 A | 3/1978 | Fey |
| 4,107,445 A | 8/1978 | Wolf et al. |
| 4,145,403 A | 3/1979 | Fey et al. |
| 4,146,389 A | 3/1979 | Karlovitz |
| 4,164,553 A * | 8/1979 | Perugini et al. ............ 423/440 |
| 4,182,746 A | 1/1980 | Myint |
| 4,309,359 A | 1/1982 | Pinto |
| 4,315,893 A | 2/1982 | McCallister |
| 4,335,080 A * | 6/1982 | Davis et al. ................ 422/244 |
| 4,347,060 A | 8/1982 | Blizzard et al. |
| 4,356,029 A | 10/1982 | Down et al. |
| 4,410,358 A | 10/1983 | Heshmatpour |
| 4,561,883 A | 12/1985 | Mullner et al. |
| 4,610,718 A | 9/1986 | Araya et al. |
| 4,610,857 A * | 9/1986 | Ogawa et al. ............... 423/335 |
| 4,612,045 A | 9/1986 | Shintaku |
| 4,670,359 A | 6/1987 | Beshty et al. |
| 4,731,111 A | 3/1988 | Kopatz et al. |
| 4,762,756 A | 8/1988 | Bergmann et al. |
| 4,772,315 A | 9/1988 | Johnson et al. |
| 4,783,216 A | 11/1988 | Kemp et al. |
| 4,784,841 A | 11/1988 | Hartmann et al. |
| 4,801,435 A | 1/1989 | Tylko |
| 4,833,170 A | 5/1989 | Agee |
| 4,844,837 A | 7/1989 | Heck et al. |
| 4,851,262 A | 7/1989 | McFeaters |
| 4,875,810 A | 10/1989 | Chiba et al. |
| 4,891,066 A | 1/1990 | Shimotori et al. |
| 4,909,914 A | 3/1990 | Chiba et al. |
| 4,911,805 A | 3/1990 | Ando et al. |
| 5,017,196 A | 5/1991 | Dewitz |
| 5,017,754 A | 5/1991 | Drouet et al. |
| 5,028,417 A | 7/1991 | Bhat et al. |
| 5,062,936 A | 11/1991 | Beaty et al. |
| 5,073,193 A | 12/1991 | Chaklader et al. |
| 5,110,565 A | 5/1992 | Weimer et al. |
| 5,194,128 A | 3/1993 | Beaty et al. |
| 5,215,749 A | 6/1993 | Nicoll et al. |
| 5,257,500 A | 11/1993 | Venkataramani et al. |
| 5,294,242 A | 3/1994 | Zurecki |
| 5,409,784 A | 4/1995 | Bromberg et al. |
| 5,425,332 A | 6/1995 | Rabinovich et al. |
| 5,437,250 A | 8/1995 | Rabinovich et al. |
| 5,451,738 A | 9/1995 | Alvi et al. |
| 5,481,080 A | 1/1996 | Lynum et al. |
| 5,486,313 A | 1/1996 | De Jong et al. |
| 5,500,501 A | 3/1996 | Lynum et al. |
| 5,527,518 A | 6/1996 | Lynum et al. |
| 5,538,706 A | 7/1996 | Kapoor et al. |
| 5,582,927 A | 12/1996 | Andricacos et al. |
| 5,723,505 A | 3/1998 | Chaumette et al. |
| 5,725,616 A | 3/1998 | Lynum et al. |
| 5,733,941 A | 3/1998 | Waycuilis |
| 5,749,937 A | 5/1998 | Detering et al. |
| 5,788,738 A | 8/1998 | Pirzada et al. |
| 5,851,507 A | 12/1998 | Pirzada et al. |
| 5,852,927 A | 12/1998 | Cohn et al. |
| 5,861,441 A | 1/1999 | Waycuilis |
| 5,883,138 A | 3/1999 | Hershkowitz et al. |
| 5,886,056 A | 3/1999 | Hershkowitz et al. |
| 5,887,554 A | 3/1999 | Cohn et al. |
| 5,935,293 A | 8/1999 | Detering et al. |
| 5,984,997 A | 11/1999 | Bickmore et al. |
| 6,127,645 A | 10/2000 | Titus et al. |
| 6,187,226 B1 | 2/2001 | Detering et al. |
| 6,379,419 B1 | 4/2002 | Celik et al. |
| 6,395,197 B1 | 5/2002 | Detering et al. |
| RE37,853 E | 9/2002 | Detering et al. |
| 2004/0208805 A1 | 10/2004 | Fincke et al. |

FOREIGN PATENT DOCUMENTS

| | | |
|---|---|---|
| DE | 1142159 | 1/1963 |
| DE | 269157 A1 | 12/1987 |
| DE | 293704 A5 | 4/1990 |
| EP | 0 282 291 B1 | 6/1992 |
| EP | 0 618 951 B1 | 9/1996 |
| FR | 2341389 | 2/1977 |
| FR | 2603209 | 8/1986 |
| GB | 2217699 A | 11/1989 |
| GB | 2279009 A | 12/1994 |
| JP | S30-7408 | 8/1952 |
| JP | S38-6854 | 5/1963 |
| JP | 59208005 | 11/1984 |
| JP | 61076604 | 4/1986 |
| JP | 62093302 | 4/1987 |
| JP | 62247836 | 10/1987 |
| JP | 64-038494 | 8/1989 |
| JP | 6183736 | 7/1994 |
| JP | 51-008192 | 1/1996 |
| JP | 8000990 | 1/1996 |
| RU | 322960 | 2/1975 |
| RU | 223055 | 6/1982 |
| WO | WO 93/12205 | 6/1993 |
| WO | WO 96/28577 | 9/1996 |
| WO | WO 98/19965 | 5/1998 |
| WO | WO 01/58625 A1 | 8/2001 |
| WO | WO 01/78471 A1 | 10/2001 |

OTHER PUBLICATIONS

"The INEL Plasma Research Program" Idaho National Engineering Laboratory (BP422E-R0592-1M-T). May 1992.

"Application of Nonequilibrium Gas-Dynamic Techniques to the Plasma Synthesis of Ceramic Powders", McFeaters, John S. and Moore, John J., In a book titled *Combustion and Plasma Synthesis of High Temperature Materials*, VCH Publications 1990. pp. 431-447.

Krasnov, A.N. et al., "Low Temperature Plasma in Mettalurgy".

Academy of Science of the USSR, Institute of Metallurgy Named After A. A. Baikov. Tsvetkov, J. V., "Low Temperature Plasma in Recovery Processes".

European Search Report, dated Apr. 9, 2003.

Olsen et al., "Unit Processes and Principles of Chemical Engineering," D. Van Nostrand Co., Inc., Jul. 5, 1932, pp. 1-3.

* cited by examiner

THERMAL SYNTHESIS APPARATUS

RELATED APPLICATION

This application is a divisional of U.S. patent application Ser. No. 09/781,931, filed on Feb. 12, 2001, now U.S. Pat. No. 6,821,500, issued Jan. 30, 2003, which claims priority from U.S. provisional patent application Ser. No. 60/181,488, filed on Feb. 10, 2000, the disclosures of which are herein incorporated by reference. This application is also a continuation-in-part of U.S. patent application Ser. No. 09/320,784, filed May 27, 1999, now U.S. Pat. No. 6,187,226, issued Feb. 13, 2001, which is a continuation-in-part of U.S. patent application Ser. No. 09/076,922, filed May 12, 1998, now U.S. Pat. No. 5,935,293, issued Aug. 10, 1999, which is a continuation-in-part of U.S. patent application Ser. No. 08/404,395, filed Mar. 14, 1995, issued as U.S. Pat. No. 5,749,937 on May 12, 1998, and reissued as United States Patent RE37,853 on Sep. 24, 2002, the disclosures of which are incorporated herein by reference.

CONTRACTUAL ORIGIN OF THE INVENTION

This invention was made with United States Government support under Contract No. DE-AC07-99ID 13727 awarded by the United States Department of Energy. The United States Government has certain rights in the invention.

BACKGROUND OF THE INVENTION

1. Field of the Invention

The present invention relates generally to a thermal synthesis process. In particular, the present invention relates to methods and apparatus for thermal conversion of reactants in a thermodynamically stable high temperature gaseous stream to desired end products, such as either a gas or ultrafine solid particles.

2. Relevant Technology

Natural gas (where methane is the main hydrocarbon) is a low value and underutilized energy resource in the United State. Huge reserves of natural gas are known to exist in remote areas of the continental U.S., but this energy resource cannot be transported economically and safely from those regions. Conversion of natural gas to higher value hydrocarbons has been researched for decades with limited success in today's economy. Recently, there have been efforts to evaluate technologies for the conversion of natural gas (which is being flared) to acetylene as a feed stock for commodity chemicals. The ready availability of large natural gas reserves associated with oil fields and cheap labor might make the natural gas to acetylene route for producing commodity chemicals particularly attractive in this part of the world.

Acetylene can be used as a feed stock for plastic manufacture or for conversion by demonstrated catalyzed reactions to liquid hydrocarbon fuels. The versatility of acetylene as a starting raw material is well known and recognized. Current feed stocks for plastics are derived from petrochemical based raw materials. Supplies from domestic and foreign oil reserves to produce these petrochemical based raw materials are declining, which puts pressure on the search for alternatives to the petrochemical based feed stock. Therefore, the interest in acetylene based feed stock has currently been rejuvenated.

Thermal conversion of methane to liquid hydrocarbons involves indirect or direct processes. The conventional methanol-to-gasoline (MTG) and the Fischer-Tropsch (FT) processes are two prime examples of such indirect conversion processes which involve reforming methane to synthesis gas before converting to the final products. These costly endothermic processes are operated at high temperatures and high pressures.

The search for direct catalytic conversion of methane to light olefins (e.g., $C_2H_4$) and then to liquid hydrocarbons has become a recent focal point of natural gas conversion technology. Oxidative coupling, oxyhydrochlorination, and partial oxidation are examples of direct conversion methods. These technologies require operation under elevated pressures, moderate temperatures, and the use of catalysts. Development of special catalysts for direct natural gas conversion process is the biggest challenge for the advancement of these technologies. The conversion yields of such processes are low, implementing them is costly in comparison to indirect processes, and the technologies have not been proven.

Light olefins can be formed by very high temperature (>1800° C.) abstraction of hydrogen from methane, followed by coupling of hydrocarbon radicals. High temperature conversion of methane to acetylene by the reaction $2CH_4 \rightarrow C_2H_2 + 3H_2$ is an example. Such processes have existed for a long time.

Methane to acetylene conversion processes currently use cold liquid hydrocarbon quenchants to prevent back reactions. Perhaps the best known of these is the Huels process which has been in commercial use in Germany for many years. The electric arc reactor of Huels transfers electrical energy by 'direct' contact between the high-temperature arc (15000-20000 K) and the methane feed stock. The product gas is quenched with water and liquefied propane to prevent back reactions. Single pass yields of acetylene are less than 40% for the Huels process. Overall $C_2H_2$ yields are increased to 58% by recycling all of the hydrocarbons except acetylene and ethylene.

Although in commercial use, the Huels process is only marginally economical because of the relatively low single pass efficiencies and the need to separate product gases from quench gases. Subsidies by the German Government have helped to keep this process in production.

A similar process with 9 MW reactors was built by DuPont and operated between 1963 and 1968 supplying acetylene produced from liquid hydrocarbon sources to a neoprene plant. The process was also reportedly demonstrated at the pilot-plant scale using methane feed. The plant-scale operation was limited to liquefied petroleum gas or liquid hydrocarbon distillates. The size of the DuPont pilot scale process is not reported. In the DuPont process the arc was magnetically rotated while in the original Huels process the arc is "swirl stabilized" by tangential injection of gases. In the DuPont process, all feedstock, diluted with hydrogen, passed through the arc column. In the Huels process, a fraction of the reactants are injected downstream of the arc.

Westinghouse has employed a hydrogen plasma reactor for the cracking of natural gas to produce acetylene. In the plasma reactor, hydrogen is fed into the arc zone and heated to a plasma state. The exiting stream of hot $H_2$ plasma at temperatures above 5000 K is mixed rapidly with the natural gas below the arc zone, and the electrical energy is indirectly transferred to the feed stock. The hot product gas is quenched with liquefied propane and water, as in the Huels process, to prevent back reactions. However, as with the Huels process, separation of the product gas from quench gas is needed. Recycling all of the hydrocarbons except acetylene and ethylene has reportedly increased the overall yield to 67%. The $H_2$ plasma process for natural gas conversion has been extensively tested on a bench scale, but further development and demonstration on a pilot scale is required.

The Scientific and Industrial Research Foundation of Norway has developed a reactor consisting of concentric, resistance-heated graphite tubes. Reaction cracking of the methane occurs in the narrow annular space between the tubes where the temperature is 1900 to 2100 K. In operation, carbon formation in the annulus led to significant operational problems. Again, liquefied quenchant is used to quench the reaction products and prevent back reactions. As with the previous two acetylene production processes described above, separation of the product gas from quench gas is needed. The overall multiple-pass acetylene yield from the resistance-heated reactor is about 80% and the process has been tested to pilot plant levels.

Accordingly, it is desirable to improve upon the modest methane conversion efficiencies, acetylene yields, selectivities, and specific energy requirements observed in the above processes.

Titanium's properties of high corrosion resistance and strength, combined with its relatively low density, result in titanium alloys being ideally suited to many high technology applications, particularly in aerospace systems. Applications of titanium in chemical and power plants are also attractive.

Unfortunately, the widespread use of titanium has been severely limited by its high cost. The magnitude of this cost is a direct consequence of the batch nature of the conventional Kroll and Hunter processes for metal production, as well as the high energy consumption rates required by their usage.

The large scale production processes used in the titanium industry have been relatively unchanged for many years. They involve the following essential steps: (1) Chlorination of impure oxide ore, (2) purification of $TiCl_4$ (3) reduction by sodium or magnesium to produce titanium sponge, (4) removal of sponge, and (5) leaching, distillation and vacuum remelting to remove Cl, Na, and Mg impurities. The combined effects of the inherent costs of such processes, the difficulty associated with forging and machining titanium and, in recent years, a shortfall in sponge availability, have contributed to relatively low titanium utilization.

One of the most promising techniques currently undergoing development to circumvent the high cost of titanium alloy parts is powder metallurgy for near net shape fabrication. For instance, it has been estimated that for every kilogram of titanium presently utilized in an aircraft, 8 kilograms of scrap are created. Powder metallurgy can substantially improve this ratio. Although this technology essentially involves the simple steps of powder production followed by compaction into a solid article, considerable development is currently underway to optimize the process such that the final product possesses at least equal properties and lower cost than wrought or cast material.

One potential powder metallurgy route to titanium alloy parts involves direct blending of elemental metal powders before compaction. Presently, titanium sponge fines from the Kroll process are used, but a major drawback is their high residual impurity content (principally chlorides), which results in porosity in the final material. The other powder metallurgy alternative involves direct use of titanium alloy powder subjected to hot isostatic pressing.

Several programs are currently involved in the optimization of such titanium alloy powders. Results are highly promising, but all involve Kroll titanium as a starting material. Use of such existing powders involves a number of expensive purification and alloying steps as outlined above.

The formation of titanium under plasma conditions has received intermittent attention in the literature over the last 30 years. Reports have generally been concerned with the hydrogen reduction of titanium tetrachloride or titanium dioxide with some isolated references to sodium or magnesium reduction.

The use of hydrogen for reducing titanium tetrachloride has been studied in an arc furnace. Only partial reduction took place at 2100 K. The same reaction system has been more extensively studied in a plasma flame and patented for the production of titanium subchloride (German Patent 1,142, 159, Jan. 10, 1963) and titanium metal (Japanese Patents 6854, May 23, 1963; 7408, Oct. 15, 1955; U.S. Pat. No. 3,123,464, Mar. 3, 1964).

Although early thermodynamic calculations indicated that the reduction of titanium tetrachloride to metallic titanium by hydrogen could start at 2500 K, the system is not a simple one. Calculations show that the formation of titanium subchloride would be thermodynamically more favorable in that temperature region.

U.S. Pat. No. 3,123,464, discloses that reduction of titanium tetrachloride to liquid titanium can be successfully carried out by heating the reactants ($TiCl_4$ and $H_2$) at least to, and preferably in excess of, the boiling point of titanium (3535 K). At such a high temperature, it was disclosed that while titanium tetrachloride vapor is effectively reduced by atomic hydrogen, the tendency of $H_2$ to dissolve in or react with Ti is insignificant, the HCl formed is only about 10% dissociated, and the formation of titanium subchlorides could be much less favorable. The titanium vapor product is then either condensed to liquid in a water-cooled steel condenser at about 3000 K, from which it overflows into a mold, or is flash-cooled by hydrogen to powder, which is collected in a bin. Since the liquid titanium was condensed from gas with only gaseous by-products or impurities, its purity, except for hydrogen, was expected to be high.

Japanese Patent 7408, describes reaction conditions as follows: a mixture of $TiCl_4$ gas and $H_2$ (50% in excess) is led through a 5 mm inside diameter nozzle of a tungsten electrode at a rate of $4 \times 10-3$ m3/min and an electric discharge (3720 V and 533 mA) made to another electrode at a distance of 15 mm. The resulting powdery crystals are heated in vacuo to produce 99.4% pure titanium.

In neither of the above patents is the energy consumption clearly mentioned. Attempts to develop the hydrogen reduction process on an industrial scale were made using a skull-melting furnace, but the effort was discontinued. More recently, a claim was made that a small quantity of titanium had been produced in a hydrogen plasma, but this was later retracted when the product was truly identified as titanium carbide.

In summary, the history of attempts to treat $TiCl_4$ in hydrogen plasmas appears to indicate that only partial reduction, i.e., to a mixture of titanium and its subchlorides, is possible unless very high temperatures (>4000 K) are reached. Prior researchers have concluded that extremely rapid, preferential condensation of vapor phase titanium would be required in order to overcome the unfavorable thermodynamics of the system.

Accordingly, there is a need for methods and apparatus that overcome or avoid the above problems and limitations.

SUMMARY AND OBJECTS OF THE INVENTION

It is an object of the invention to provide a method and apparatus for thermal conversion of one or more reactants in a thermodynamically stable high temperature gaseous stream to a desired end product.

It is a further object of the invention to provide an improved process conversion efficiency and product yield in the thermal conversion of one or more reactants in a thermodynamically stable high temperature gaseous stream to a desired end product.

It is yet another object of the invention to provide a method and apparatus for increasing acetylene yield from the thermal conversion of natural gas.

To achieve the foregoing objects, and in accordance with the invention as embodied and broadly described herein, a method and apparatus are provided for thermal conversion of one or more reactants in a thermodynamically stable high temperature gaseous stream to a desired end product in the form of a gas or ultrafine solid particles. In general, the method includes the following steps. First, a reactant stream is introduced at one end of an axial reactor. Next, the reactant stream is heated as the reactant stream flows axially through an injection line having a reduced diameter with respect to the axial reactor to produce turbulent flow and thereby thoroughly mix the reactant stream with a heating gas. Thereafter, the thoroughly mixed reactant stream is passed axially through a reaction zone of the axial reactor, with the reaction zone maintained at a substantially uniform temperature over the length of the reaction zone. The axial reactor has a length and a temperature and is operated under conditions sufficient to effect heating of the reactant stream to a selected reaction temperature at which a desired product stream is produced at a location adjacent the outlet end of the axial reactor.

In particular, the method of the invention comprises the following steps. First, a stream of plasma arc gas is introduced between the electrodes of a plasma torch including at least one pair of electrodes positioned adjacent to an inlet end of an axial reactor chamber. The stream of plasma arc gas is introduced at a selected plasma gas flow while the electrodes are subjected to a selected plasma input power level to produce a plasma in a restricted diameter injection line that extends into the reactor chamber and toward an outlet end of the reactor chamber. Second, an incoming reactant stream is thoroughly mixed into the plasma by injecting at least one reactant into the injection line to produce the thorough mixing prior to introduction into the reactor chamber. The reactor chamber is maintained at a substantially uniform temperature over the flow field for the reactions to reach equilibrium. The gaseous stream exiting a nozzle is cooled at the outlet end of the reactor chamber by reducing its velocity while removing heat energy at a rate sufficient to prevent increases in its kinetic temperature. The desired end products are then separated from the gases remaining in the cooled gaseous stream.

The present invention provides improvements in process conversion efficiency and acetylene yield over prior conventional processes. Such improvements are primarily accomplished by more efficient injection and mixing of reactants with plasma gases, and minimization of temperature gradients and cold boundary layers in the reactor. The improved mixing and thermal control also leads to increased specificity reducing the yield of hydrocarbons other than acetylene. The quench rate achieved by wall heat transfer in small reactors is adequate to arrest acetylene decomposition and soot formation. Formation of other hydrocarbon species, except for ethylene, is unaffected by significantly increasing the quench rate.

These and other objects, features, and advantages of the present invention will become more fully apparent from the following description and appended claims, or may be learned by the practice of the invention as set forth hereinafter.

BRIEF DESCRIPTION OF THE DRAWINGS

In order to illustrate the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
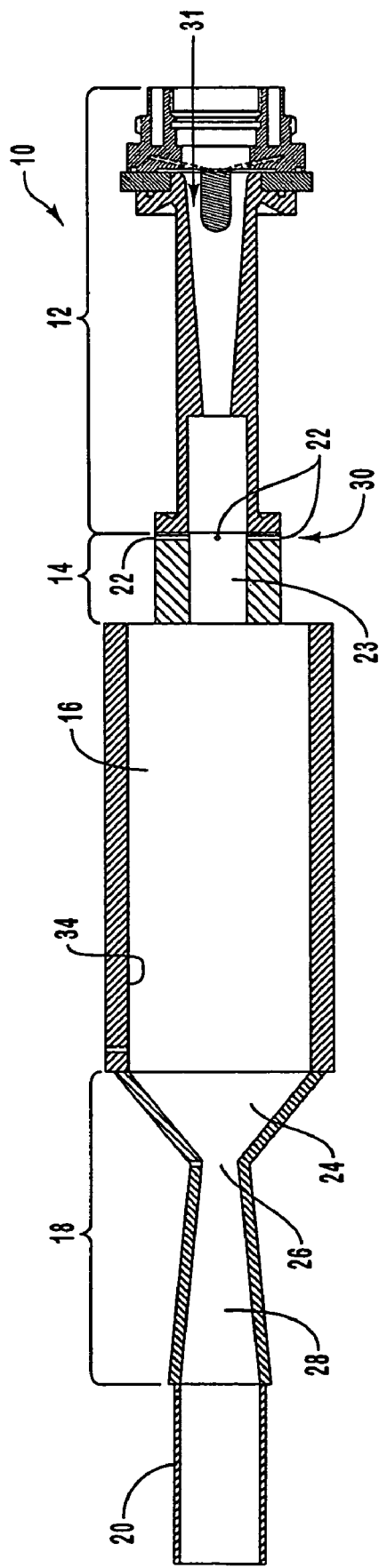
FIG. 1 is a schematic cross-sectional view of a reactor system according to one embodiment of the invention.

The present invention relates generally to methods and apparatus for thermal conversion of reactants to desired end products, such as either a gas or ultrafine solid particles. Generally, an apparatus according to the present invention includes a multi-port injector that injects the reactants into a chamber upstream from a reactor and thereby allows the reactants to mix with a plasma stream. The reactor is insulated, such as with a carbon lining, which provides residence time for reactions to take place while minimizing radial temperature gradients. Optionally, a converging-diverging nozzle is attached at the outlet end of the reactor, which provides for supersonic expansion to greatly increase quench rates.

Various reactors and methods for high temperature reactions that require rapid cooling to freeze the reaction products to prevent back reactions or decompositions to undesirable products exist. For example, U.S. Pat. No. 5,749,937 to Detering (hereinafter "Detering") herein expressly incorporated by reference, uses adiabatic and isentropic expansion of gases in a converging-diverging nozzle for rapid quenching. This expansion can result in cooling rates exceeding 1010 K/s, thus preserving reaction products that are in equilibrium only at high temperatures.

Nevertheless, there is a continuing need for improved conversion efficiency and yield values. It has been discovered that temperature gradients and poor mixing lead to a non-uniform distribution of temperatures in reactors. The composition of the product stream is a function of kinetics or rate of reaction and also of the temperature non-uniformities. These effects can lead to significant variations in product stream composition. If the quench process is too slow or delayed, the product produced, such as acetylene, can thermally decompose to solid carbon soot or may further react, principally on hot surfaces, to form benzene and heavier hydrocarbons.

These problems are addressed by the present invention. The problem of non-uniform temperatures is overcome by using an insulatively lined "hot wall" reactor configuration, such as a carbon lined reactor, which minimizes the radial temperature gradients and heat loss from the reactor section. The problem of poor mixing is addressed through the use of a confined channel injector design, which provides good mixing of reactants into a plasma stream. The effect of quench rate is addressed by the incorporation of a supersonic quench nozzle into the apparatus, just downstream of the reactor section. In the supersonic nozzle, the hot gases in the reactor section are rapidly expanded to a lower pressure. Thus, thermal energy is converted to kinetic energy and the mixture is rapidly cooled. This process is sometimes referred to as an aerodynamic quench. Quench rates of 107°-108° C./s or two to three orders of magnitude greater than those reported in the original Huels process are achievable. Without the converging-diverging nozzle, quench rates by wall heat transfer are estimated to be on the order of 0.1×106° C./s.

Although the concepts of this reactor were originally developed in a study of the formation of acetylene from natural gas, it will be appreciated by one skilled in the art that the methods and apparatus of the invention can be used for other processes requiring rapid quenching, including the production of titanium.

The fast quench reactor and method of operation described herein take advantage of the high temperatures (5,000° to 20,000° C.) available in a high temperature heating means such as a thermal plasma device to produce materials that are thermodynamically stable at these high temperatures. These materials include metals, alloys, intermetallics, composites, gases and ceramics.

The fast quench reactor and method of this invention shall be described and illustrated forthwith in terms of a rapid heating means comprising a plasma torch and a stream of plasma arc gas. However, it will be recognized that the rapid heating means can also include other rapid heating means such as lasers, and flames produced by oxidation of a suitable fuel, e.g., an oxygen/hydrogen flame.

It will be appreciated that the various features described hereinbelow in the various embodiments can be interchanged to provide further embodiments that are encompassed by the present invention. For example, various embodiments may or not have a converging-diverging nozzle, mixing chamber, downstream injector, or anode injector.

Referring now to the drawings, FIG. 1 is a schematic diagram of an ultra fast quenching apparatus 10. The apparatus 10 generally includes a torch section 12, an injector section 14, an enclosed axial reactor chamber 16, a converging-diverging nozzle 18, and a cooling section 20.

In one embodiment of the invention, the apparatus 10 is a fast quench axial reactor for thermal conversion of one or more reactants in a thermodynamically stable high temperature gaseous stream to a desired end product in the form of a gas or ultrafine solid particles. The apparatus 10 includes means for introducing a reactant stream at or upstream from an inlet end of the axial reactor, such as a multi-port injector located in either injector section 14 or torch section 12 or an anode injector as described hereinbelow, or equivalents thereof. The apparatus 10 also includes a heating means for producing a hot gaseous stream upstream from the inlet end of the axial reactor, wherein the stream is flowing axially toward an outlet end of the axial reactor. Such heating means can be selected from a plasma generating torch, lasers, flames produced by oxidation of a suitable fuel, e.g., an oxygen/hydrogen flame, and equivalents thereof. Further, apparatus 10 includes means for passing the reactant stream and the hot gaseous stream through an injection line having a reduced diameter to produce turbulent flow and thereby thoroughly mix the reactant stream with the hot gaseous stream, such as an injection line 23 in injector section 14 or in torch section 12, or equivalents thereof. Apparatus 10 further includes means for minimizing radial temperature gradients within the axial reactor, such as an insulating layer on the interior of reactor chamber 16, and equivalents thereof. The axial reactor is preferably operated under conditions sufficient to effect heating of the reactant stream to a selected reaction temperature at which a desired end product is produced at a location adjacent the outlet end of the axial reactor. The various components of apparatus 10 will be described in further detail hereafter The torch section 12 includes a plasma torch that is used to thermally decompose an incoming gaseous stream within a resulting plasma as the gaseous stream is delivered through the inlet of the reactor chamber.

A plasma is a high temperature luminous gas which is at least partially (1 to 100%) ionized. A plasma is made up of gas atoms, gas ions, and electrons. In the bulk phase a plasma is electrically neutral. A thermal plasma can be created by passing a gas through an electric arc formed between two electrodes (anode and cathode). The electric arc will rapidly heat the gas by resistive and radiative heating to very high temperatures within microseconds of passing through the arc. The plasma is typically luminous at temperatures above 9000 K.

A plasma can be produced with any gas in this manner. This gives excellent control over chemical reactions in the plasma as the gas might be neutral (argon, helium, neon), reductive (hydrogen, methane, ammonia, carbon monoxide) or oxidative (oxygen, nitrogen, carbon dioxide). Oxygen or oxygen/argon gas mixtures are used to produce metal oxide ceramics and composites. Other nitride, boride, and carbide ceramic materials require gases such as nitrogen, ammonia, hydrogen, methane, or carbon monoxide to achieve the correct chemical environment for synthesis of these materials.

The details of plasma generating torches are well known and need not be further detailed within this disclosure to make the present invention understandable to those skilled in this field.

An incoming stream of plasma gas is denoted by arrow 31. The plasma gas can also be a reactant or can be inert. A gaseous stream of one or more reactants (arrow 30) is normally injected separately into the plasma, which is directed toward the downstream outlet of the reactor chamber 16. The gaseous stream moving axially through the reactor chamber 16 includes the reactants injected into the plasma arc or within a carrier gas.

The injector section 14 includes injection ports 22, and a restricted diameter injection line 23 allows the reactants and plasma to mix before the reactant materials enter the reactor chamber 16. By allowing the reactants and plasma to mix prior to entering the reactor 16, there is less heat loss and the system efficiency improves.

Gases and liquids are the preferred forms of injected reactants. Solids may be injected, but usually vaporize too slowly for chemical reactions to occur in the rapidly flowing plasma gas before the gas cools. If solids are used as reactants, they will usually be heated to a gaseous or liquid state before injection into the plasma.

Typical residence times for materials within the free flowing plasma are on the order of milliseconds. To maximize mixing with the plasma gas, the reactants (liquid or gas) are injected under pressure (10 to 100 atmospheres) through a small orifice to achieve sufficient velocity to penetrate and mix with the plasma. It is preferable to use gaseous or vaporized reactants whenever practical, since this eliminates the need for a phase change within the plasma and improves the kinetics of the reactor. In addition, the injected stream of reactants is preferably is injected normal (90° angle) to the flow of the plasma gases. In some cases, however, positive or negative deviations from this 90° angle by as much as 30° may be optimum.

The high temperature of the plasma rapidly vaporizes the injected liquid materials and breaks apart gaseous molecular species to their atomic constituents. A variety of metals (titanium, vanadium, antimony, silicon, aluminum, uranium, tungsten), metal alloys (titanium/vanadium, titanium/aluminum, titanium/aluminum/vanadium), intermetallics (nickel aluminide, titanium aluminide), and ceramics (metal oxides, nitrides, borides, and carbides) can be synthesized by injecting metal halides (chlorides, bromides, iodides, and fluorides) in liquid or gaseous form into a plasma of the appropriate gas downstream from the anode arc attachment point and within the torch exit or along the length of the reactor chamber.

The enclosed axial reactor chamber 16 communicates with injector section 14 at an inlet end and communicates with nozzle 18 at an outlet end. The reactor chamber 16 according to on embodiment of the invention includes an insulative liner 34 on the interior surface thereof. The insulated reactor provides residence time for reactions to take place while minimizing radial temperature gradients. A cooling water jacket (not shown) is typically disposed around the outside of reactor chamber 16.

The reactor chamber 16 is the location in which chemical reactions occur. The reactor chamber 16 begins downstream from the plasma arc inlet and terminates at the nozzle throat 26. The reactor chamber 16 includes a main reactor area in which product formation occurs, as well as a converging section 24, which is part of nozzle 18.

Temperature requirements within the reactor chamber and its dimensional geometry are specific to the temperature required to achieve an equilibrium state with an enriched quantity of each desired end product.

Since the reaction chamber is an area of intense heat and chemical activity it is necessary to construct the reactor chamber of materials that are compatible with the temperature and chemical activity to minimize chemical corrosion from the reactants, and to minimize melting degradation and ablation from the resulting intense plasma radiation. The reactor chamber is usually constructed of water cooled stainless steel, nickel, titanium, or other suitable materials. The reactor chamber can also be constructed of ceramic materials to withstand the vigorous chemical and thermal environment.

As discussed previously, the reactor chamber walls are lined with an insulator, such as carbon, to maintain a constant temperature gradient within the reactor chamber 16. The purpose of the insulator is to provide a barrier to reduce process heat loss to the cooling water jacket on the outside of the reactor chamber. Various insulative materials can be utilized as long as the selected material does not react with the reactants in the reactor chamber and has a sufficiently low coefficient of expansion to prevent swelling and bursting of the outer wall of the reactor chamber. Thus, preferred materials such as carbon are good insulators, are chemically inert to the process reactants, have a low expansion coefficient, and withstand high temperatures, such about 2000° to 3000° K. Other suitable materials include, for example, boron nitride, zirconia, silicon carbide, and the like. However, any insulating material that will reduce heat transfer from the reactor chamber 16 to the outside wall will work as long as the above criteria is met.

The reaction chamber walls are internally heated by a combination of radiation, convection and conduction. Cooling of the reaction chamber walls prevents unwanted melting and/or corrosion at their surfaces. The system used to control such cooling should maintain the walls at as high a temperature as can be permitted by the selected wall material, which must be inert to the reactants within the reactor chamber 16 at the expected wall temperatures. This is true also with regard to the nozzle walls, which are subjected to heat only by convection and conduction.

The dimensions of the reactor chamber 16 are chosen to minimize recirculation of the plasma and reactant gases and to maintain sufficient heat (enthalpy) going into the nozzle throat to prevent degradation (undesirable back or side reaction chemistry).

The length of the reactor chamber 16 must be determined experimentally by first using an elongated tube within which the user can locate the target reaction threshold temperature. The reactor chamber 16 can then be designed long enough so that reactants have sufficient residence time at the high reaction temperature to reach an equilibrium state and complete the formation of the desired end products. Such reaction temperatures can range from a minimum of about 1700° C. to about 4000° C.

The inside diameter of the reactor chamber 16 is determined by the fluid properties of the plasma and moving gaseous stream. It must be sufficiently great to permit necessary gaseous flow, but not so large that undesirable recirculating eddies or stagnant zones are formed along the walls of the chamber. Such detrimental flow patterns will cool the gases prematurely and precipitate unwanted products, such as subchlorides or carbon. As a general rule, the inside diameter of the reactor chamber 16 should be in the range of about 100 to about 150% of the plasma diameter at the inlet end of the reactor chamber 16.

The convergent-diverging nozzle 18 is coaxially positioned downstream from reactor chamber 16. The converging-diverging nozzle produces a rapid drop in kinetic temperature in a flowing gas stream. This effectively "freezes" or stops all chemical reactions. It permits efficient collection of desired end products as the gases are rapidly cooled without achieving an equilibrium condition. Resulting end products which have been produced in the plasma at high temperature but are thermodynamically unstable or unavailable at lower temperatures can then be collected due to resulting phase changes (gas to solid) or stabilization by cooling to a lower equilibrium state (gas to gas).

The converging or upstream section of nozzle 18 restricts gas passage and controls the residence time of the hot gaseous stream within the reactor chamber 16, allowing its contents to reach thermodynamic equilibrium. The contraction that occurs in the cross sectional size of the gaseous stream as it passes through the converging portions of nozzle 18 change the motion of the gas molecules from random directions, including rotational and vibrational motions, to straight line motion parallel to the reactor chamber axis. The dimensions of the reactor chamber 16 and the incoming gaseous flow rates are selected to achieve sonic velocity within the restricted nozzle throat.

As the confined stream of gas enters the diverging or downstream portions of nozzle 18, it is subjected to an ultra fast decrease in pressure as a result of a gradual increase in volume along the conical walls of the nozzle exit. The resulting pressure change instantaneously lowers the temperature of the gaseous stream to a new equilibrium condition.

By proper selection of nozzle dimensions, the reactor chamber 16 can be operated at atmospheric pressure or in a pressurized condition, while the cooling section 20 downstream from nozzle 18 is maintained at a vacuum pressure by operation of a pump. The sudden pressure change that occurs as the gaseous stream traverses nozzle 18 brings the gaseous stream to a lower equilibrium condition instantly and prevents unwanted back reactions that would occur under more drawn out cooling conditions.

The purpose of the converging section 24 of the nozzle 18 is to compress the hot gases rapidly into a restrictive nozzle throat 26 with a minimum of heat loss to the walls while maintaining laminar flow and a minimum of turbulence. This requires a high aspect ratio change in diameter that maintains smooth transitions to a first steep angle (>45°) and then to lesser angles (<45°) leading into the nozzle throat.

The purpose of the nozzle throat 26 is to compress the gases and achieve sonic velocities in the flowing hot gaseous stream. This converts the random energy content of the hot gases to translational energy (velocity) in the axial direction of gas flow. This effectively lowers the kinetic temperature of the gases and almost instantaneously limits further chemical reactions. The velocities achieved in the nozzle throat and in the downstream diverging section of the nozzle are controlled by the pressure differential between the reactor chamber 16 and the section downstream of the diverging section 28 of nozzle 18. Negative pressure can be applied downstream or positive pressure applied upstream for this purpose.

The purpose of the diverging section 28 of nozzle 18 is to smoothly accelerate and expand gases exiting the nozzle from sonic to supersonic velocities, which further lowers the kinetic temperature of the gases.

The term "smooth acceleration" in practice requires use of a small diverging angle of less than 35 degrees to expand the gases without suffering deleterious effects of separation from the converging wall and inducing turbulence. Separation of the expanding gases from the diverging wall causes recirculation of some portion of the gases between the wall and the gas jet exiting the nozzle throat. This recirculation in turn results in local reheating of the expanding gases and undesirable degradation reactions, producing lower yields of desired end products.

The super fast quench phenomenon observed in the embodiments of the invention that include a converging-diverging nozzle in the apparatus is achieved by rapidly converting thermal energy in the gases to kinetic energy via a modified adiabatic and isentropic expansion through the converging-diverging nozzle. A thorough discussion of the physics of the nozzle is provided in Detering.

An additional reactant, such as hydrogen at ambient temperatures, can be tangentially injected into the diverging section of nozzle 18 to complete the reactions or prevent back reactions as the gases are cooled.

Cooling section 20 is positioned coaxially downstream from nozzle 18 and serves to further cool the gaseous stream and quench the reactions. The walls of reactor chamber 16, nozzle 18, and coaxial cooling section 20 are all physically cooled by cooling streams.

Reaction end products are collectable within a cyclone separator (not shown). A downstream liquid trap, such as a liquid nitrogen trap, can be used to condense and collect reaction products such as hydrogen chloride and ultra-fine powders within the gaseous stream prior to the gaseous stream entering a vacuum pump.

Figure 2:
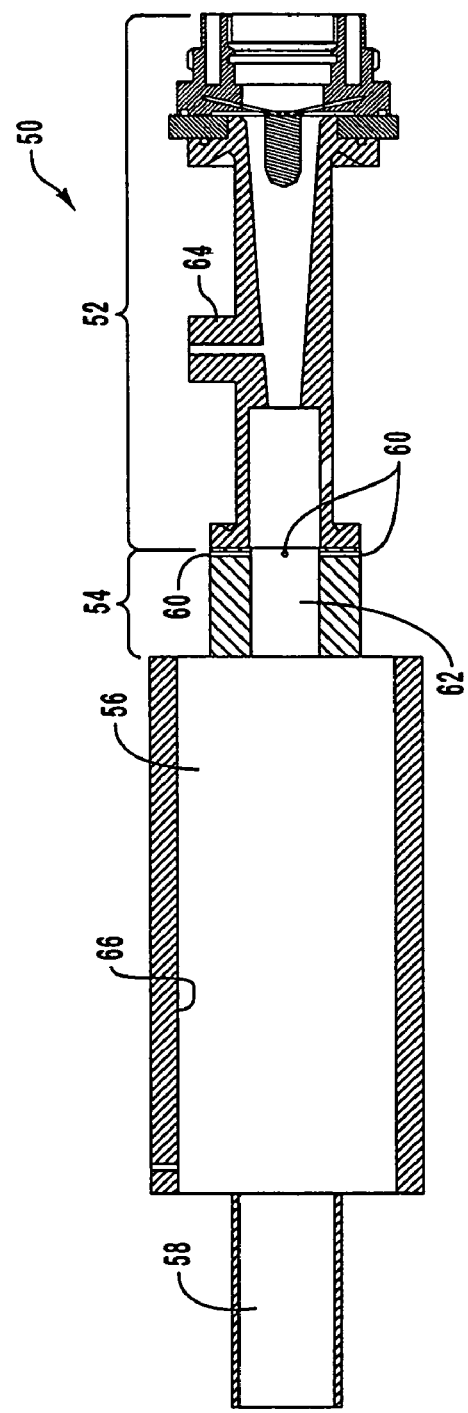
FIG. 2 is a schematic cross-sectional view of a reactor system according to another embodiment of the invention.

Referring now to FIG. 2, a further embodiment of the invention comprises an apparatus 50, which includes generally a torch/injection section 52, an injector section 54, a insulated reactor chamber 56, and a cooling section 58. It is understood that the majority of the components are as described hereinabove for apparatus 10.

It has been discovered that the various improvements described hereinabove make nozzle 18 unnecessary to obtain positive results in this embodiment of the invention. Accordingly, the nozzle assembly is removed and replaced with a straight cooling pipe section of the same inside diameter as the downstream piping. Although not illustrated, the present invention also anticipates that the nozzle assembly can be replaced by a converging section similar to the converging section 24 of converging-diverging nozzle 18 when solid material plugging is to be avoided. If this is not a problem, then the abrupt transition from reactor chamber 56 to cooling section 58 is suitable.

Yet another feature of this embodiment of the invention is that an anode injector 64 is included as part of torch/injection section 52. By locating anode injector 64 closer to the plasma arc, there is reduced heat loss and therefore greater mixing efficiency. However, this embodiment also illustrates that a downstream injector port(s) 60 can also be included, providing a separate reactant injection port in communication with injection line 62.

The reactor chamber 56 according to this embodiment of the invention includes an insulative liner 66 on the interior surface thereof.

Figure 3:
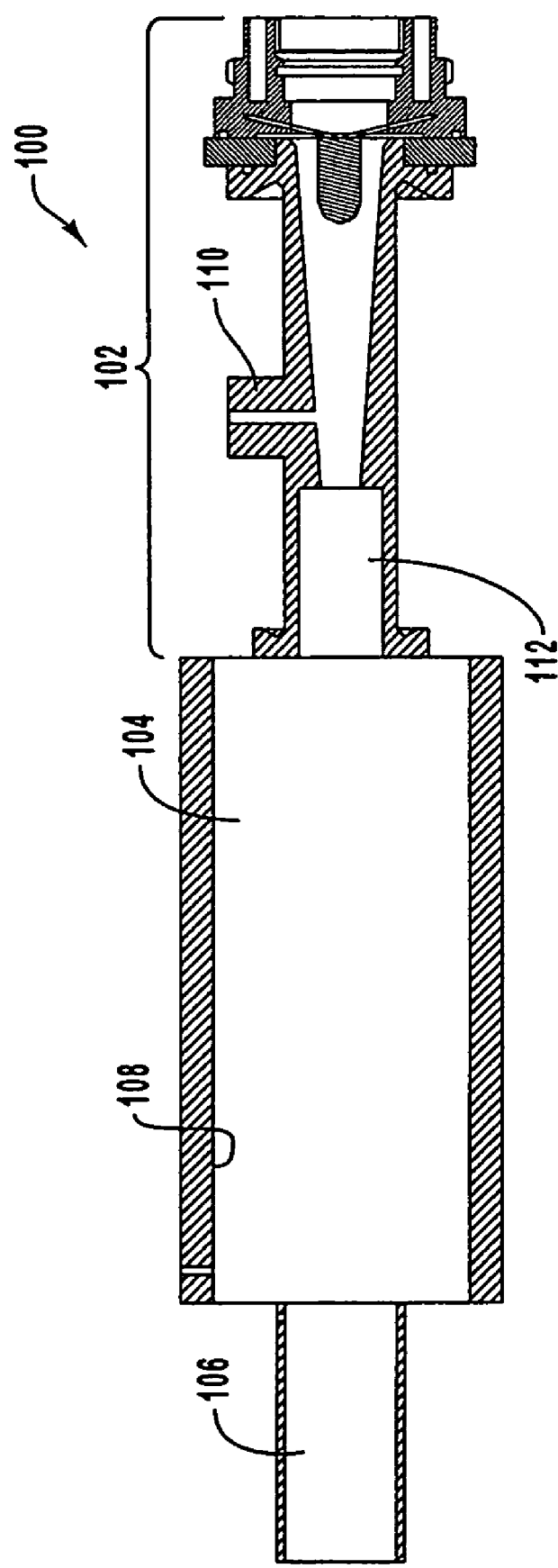
FIG. 3 is a schematic cross-sectional view of a reactor system according to a further embodiment of the invention.

Referring now to FIG. 3, another embodiment of the invention comprises an apparatus 100, which includes generally a torch/injection section 102, an insulated reactor chamber 104, and a cooling section 106. In particular, this embodiment eliminates the injector section used in the embodiments described hereinabove. It is understood that the majority of the components are as described hereinabove for apparatus 10.

The apparatus 100 includes an anode injector 110, but no downstream injector. As a result, the anode injector 110 is close to the arc, has space to provide a thorough mixing prior to entering the reaction chamber, and is closer to the reaction chamber to avoid excess cooling. However, it can be seen that torch section 102 still includes a reduced diameter injection line 112 to create turbulant flow and to ensure that the reactants thoroughly mix with the plasma before entering the reactor chamber 104.

It is by including insulating layer 108 on reactor chamber 104, including injection line 112, and by carefully placing anode injector 110 closer to the arc that apparatus 100 is able to achieve the desired reactions at a high efficiency, even without the converging-diverging nozzle.

Although the present disclosure focuses on the production of acetylene from methane, it will understood by those skilled in the art that other materials can also be produced by the methods and apparatus of the invention. These include, by way of example only, titanium, vanadium, aluminum, and titanium/vanadium alloys.

The following examples are given to illustrate the present invention, and are not intended to limit the scope of the invention.

EXAMPLES

All instrumentation used in the following Examples except for the gas chromatograph (GC) was directly interfaced to a data acquisition system for continuous recording of system parameters during a test run. Once the specified process power levels, pressure, and gas flow rates were established, the gas stream was continuously sampled by the gas chromatograph for a period of 7 minutes before the chromatograph gas sample was acquired to ensure that a representative sample was obtained. This sampling period represents approximately three times the time required to completely purge the sample line. The pressure downstream of the quench nozzle was controlled by a mechanical vacuum pump and flow control valve. Depending on the test conditions, the test pressure can be independently adjusted between atmospheric pressure and approximately 100 torr. The experiment reached steady state in a period of 1 minute or less. Steady state operation was verified by a continuously reading residual gas analyzer (RGA). All cooling water flow rates and inlet and outlet temperatures were monitored and recorded allowing a complete system energy balance to be calculated.

The plasma gases used were a mixture of Ar and $H_2$; methane or natural gas was injected downstream in a confined channel transverse jet injector. The DC plasma torch that was used will not operate for extended periods of time on pure hydrogen without severe anode erosion, hence all test data was acquired using at least some Ar plasma gas. The use of Ar, which is inert and does not participate chemically in the process, has the advantage that it provides a built-in reference for validating the overall process mass balance. The processing of methane directly in the discharge is precluded by the severe erosion of the tungsten cathode via the formation of volatile tungsten carbides. The two most critical aspects of the experiment are the chemical analysis of the product stream and the overall mass balance.

Two example test series were conducted, with the major differences between the two being the presence or absence of the converging-diverging quench nozzle. When the quench nozzle was installed, a downstream valve was wide open and the downstream pressure was determined by the capacity of a vacuum pump. The downstream pressure in this mode generally ran between 100 and 200 torr. In this configuration, the flow was choked in the converging-diverging nozzle throat and the reactor pressure was determined by the nozzle throat diameter, the reactor temperature, and the mass flow rate of the plasma and reactant gases. Under these conditions the reactor pressure generally ran between 600 and 800 torr for an upstream to downstream pressure ratio between 4 and 6. The corresponding Mach number range was 1.6 to 1.8. Assuming a reactor temperature of 2000° C., the aerodynamic quench rapidly lowers the temperature to 1100-1300° C. The measured thermal efficiency of the plasma torch was between 80 and 90% depending on the gas mixture and flow rates. The power to the plasma torch was adjusted to give a constant 60 kW deposited in the plasma gas. Since the torch voltage is essentially determined by the argon to hydrogen ratio, the power was adjusted by adjusting the current to obtain the desired 60 kW into the plasma. The injector ring, reactor section, and nozzle assembly energy balances indicated that approximately 14.6 kW were lost in these components to the cooling water. The partitioning of this energy loss is illustrated in Table 1 below:

TABLE 1

| | Location: | | | |
|---|---|---|---|---|
| | Torch | Injector | Reactor | Nozzle |
| Energy loss: | +60 kW into plasma | −7.3 kW to cooling water | −3.9 kW to cooling water | −3.4 kW to cooling water |

Figure 4:
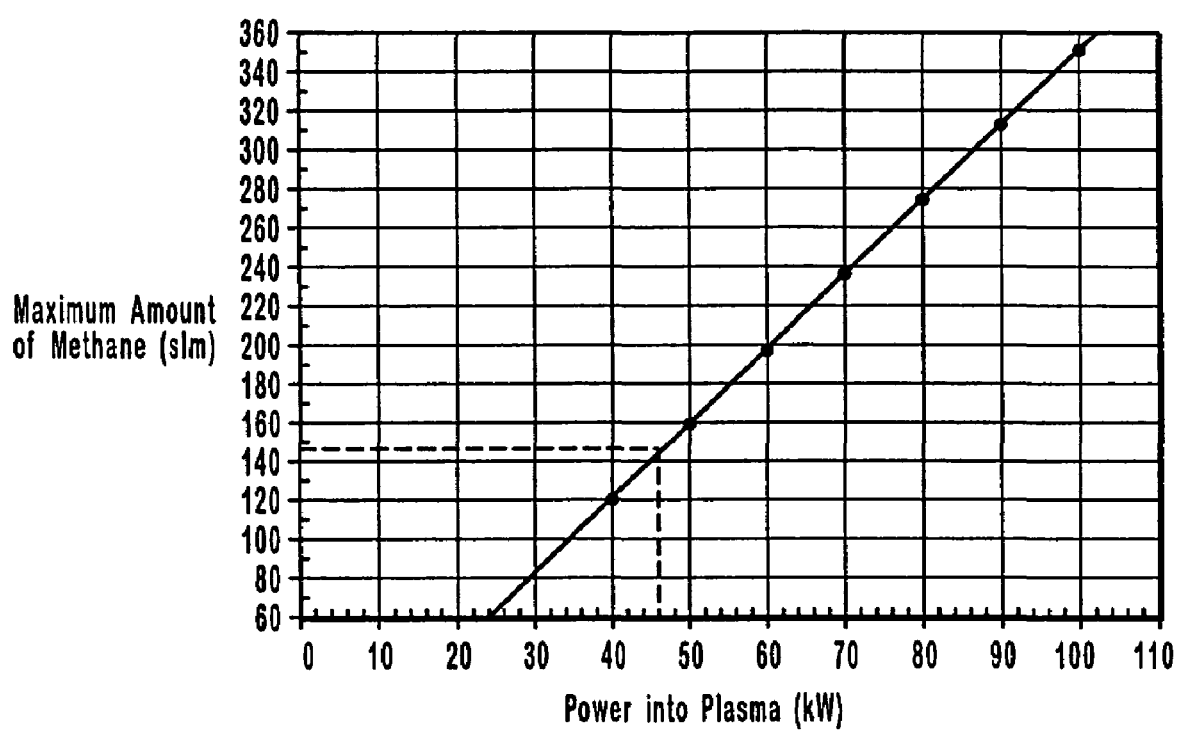
FIG. 4 is a graph plotting the theoretical maximum amount of methane that can be processed in the reactor system of the invention.

The result is that approximately 45 kW is available for conversion of natural gas to acetylene. By careful system redesign, which includes placement of the injector function inside the torch body and optimization (shortening) of reactor length, these losses can probably be reduced by 70% or more. FIG. 4 contains a plot of the theoretical maximum amount of methane that can be converted to acetylene in the current configuration under nominal operating conditions. Nominal operating conditions are defined as 160 standard liters per minute (slm) Ar, 100 slm $H_2$ for the plasma torch gas and 60 kW deposited in the plasma. The target reactor temperature is 2000° C. Under the nominal conditions the maximum theoretical amount of methane that can be converted to acetylene is approximately 145 slm.

The conversion efficiency, for pure methane injection, is defined as:

$$CE = 1 - \frac{[CH_4]\dot{Q}_{STP}}{\dot{Q}_{CH_4}} = 1 - y_{CH_4}$$

where $[CH_4]$ is the molar fraction of methane in the product stream obtained from the GC and $Q_{CH_4}$ is the methane injection rate.

Acetylene yield (for pure methane injection) is defined as:

$$y_{C_2H_2} = \frac{2[C_2H_2]\dot{Q}_{STP}}{\dot{Q}_{CH_4}}$$

where $[C_2H_2]$ is the molar fraction of acetylene in the product stream measured by the GC and the actual measured gas flow converted to standard conditions (1 atmosphere pressure and 0° C.) is $Q_{STP}$ Example 1

Figure 5:
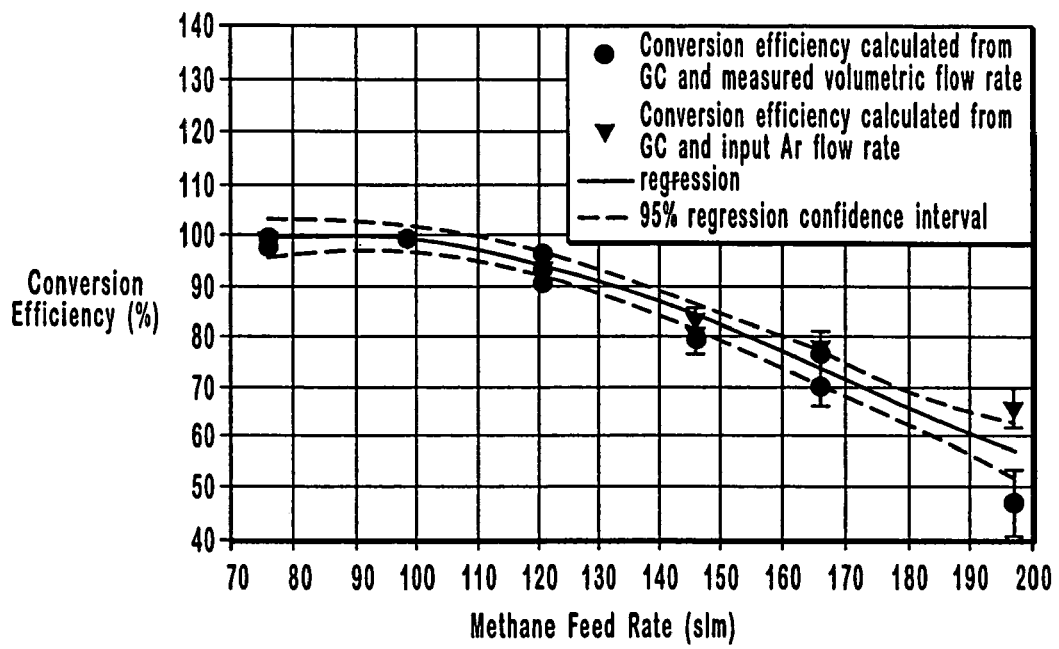
FIG. 5 is a graph plotting conversion efficiency as a function of methane feed rate.

In this example the results of experiments with a converging-diverging nozzle are presented. Conversion efficiency as a function of the rate of methane injection is plotted in the graph of FIG. 5. In developing this data set the power deposited in the plasma was maintained constant at 60 kW and the plasma gas flow rates were constant at 160 slm Ar and 100 slm $H_2$. The measured reactor pressure was relatively constant, varying between approximately 670 and 730 torr, depending on the rate of methane injection. Methane conversion was essentially complete, that is a conversion efficiency of 100%, at methane feed rates up to about 100 slm. At feed rates above 100 slm the conversion efficiency started to decline and dipped below approximately 95% at a feed rate of around 120 slm. The estimated bulk gas temperature in the reactor and corresponding residence time in the reactor is plotted in the graph of FIG. 6. This estimate was obtained from the measured system energy balance, the plasma gas and methane flow rates, and the assumption of 100% acetylene yield. The target temperature of approximately 2000° C. was reached at a methane flow rate of approximately 145 slm. For methane injection rates less than 145 slm the estimated reactor temperature was greater than 2000° C. If the reactor temperature is uniform, which it is not, and if the process follows the equilibrium diagram of the graph of FIG. 4, it is expected that for temperatures much below 2000° C. (methane feed rates greater that about 145 slm) that the conversion efficiency will start to decline.

Figure 6:
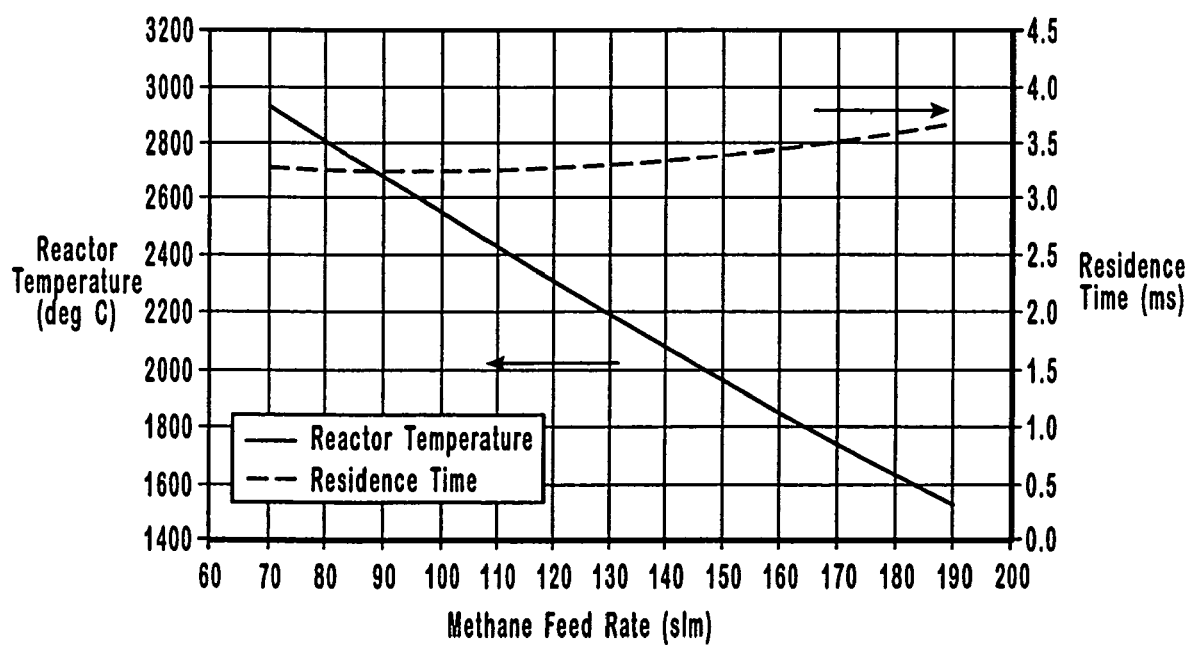
FIG. 6 is a graph plotting estimated reactor temperature and reactor residence time as a function of methane injection rate.

An alternative representation of this is shown in the graph of FIG. 4 where the maximum amount of methane that it is theoretically possible to process is plotted as a function of energy (power) available. For the nominal operating condition of 60 kW into the plasma gas minus the 15 or so kW that is lost in the injector, reactor and nozzle assembly for a net of about 45 kW, the maximum amount of methane that can be processed is approximately 145 slm. For injection rates in excess of 145 slm there was not enough energy available to dissociate and convert the injected methane to acetylene with 100% efficiency and result in a product stream temperature of 2000° C. The presence of the inevitable cold boundary layers in the injection ring and reactor also result in some gas that can pass through the reactor without being dissociated. At the lower flow rates and corresponding higher temperatures the methane was almost completely converted and the conversion efficiency approaches 100%. The conversion efficiency was observed to decline at 120 slm, somewhat below the anticipated value of 145 slm. This may be due to the presence of cold boundary layer flow, or due to inadequate residence time for dissociation. Inspection of the residence time plot in FIG. 6, shows that the residence time in the reactor is relatively constant and independent of methane injection rate. The increase in mass flow rate and anticipated velocity increase with increased methane injection is offset by the cooling of the gas mixture that also occurs with increased methane injection rate.

Figure 7:
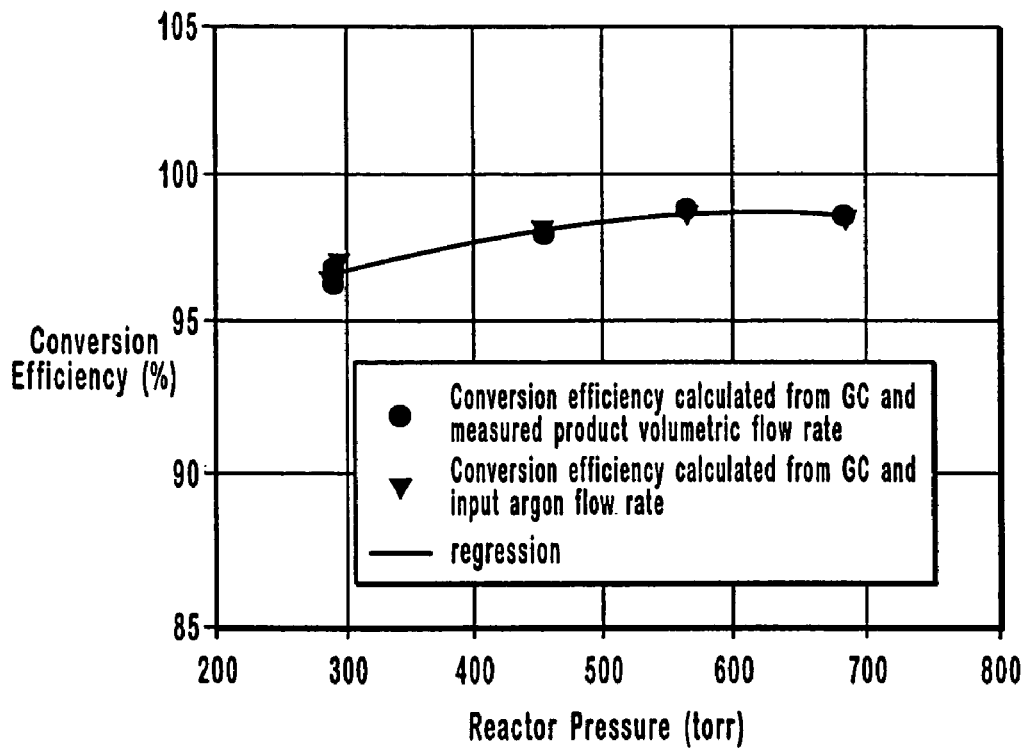
FIG. 7 is a graph plotting methane conversion efficiency as a function of reactor pressure.

The possible influence of residence time on conversion efficiency was evaluated by replacing the converging-diverging nozzle with a straight, constant diameter section that matched the inside diameter of the downstream piping. By removing the converging-diverging nozzle the reactor pressure could be controlled independently of the flow rates. When the converging-diverging nozzle is installed the flow is choked (reaches sonic velocity) in the nozzle throat. Under this condition the reactor pressure is independent of the downstream pressure and is determined solely by the mass flow rate and temperature. With the converging-diverging nozzle removed the reactor pressure is controlled by the position of a downstream valve. Decreasing the reactor pressure increases the velocity in the reactor and decreases residence time. For this series of tests the pressure was varied from 300 to 700 torr, decreasing the residence time in the reactor by a factor of 2.3, or from about 3.25 ms to 1.4 ms. A slight decrease in conversion efficiency of about 2 percentage points, was observed at the lower pressure, as shown in the graph of FIG. 7. While this suggests a slight dependence on residence time it is not enough to account for the decrease in conversion efficiency observed in the graph of FIG. 5. This suggests that the presence of cold boundary layers is in fact mostly responsible for the observed decrease. The residence time in the reactor is sufficient for dissociation of the methane, and as we will show next, also sufficient for the formation of acetylene.

Figure 8:
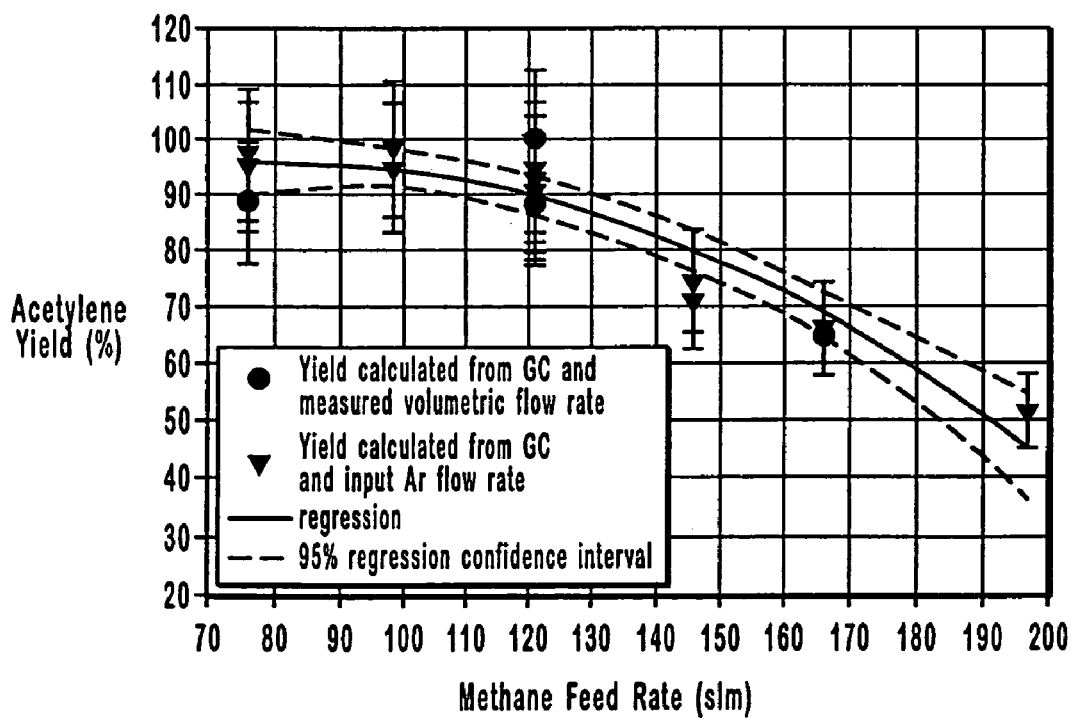
FIG. 8 is a graph plotting acetylene yield as a function of methane injection rate.
Figure 9:
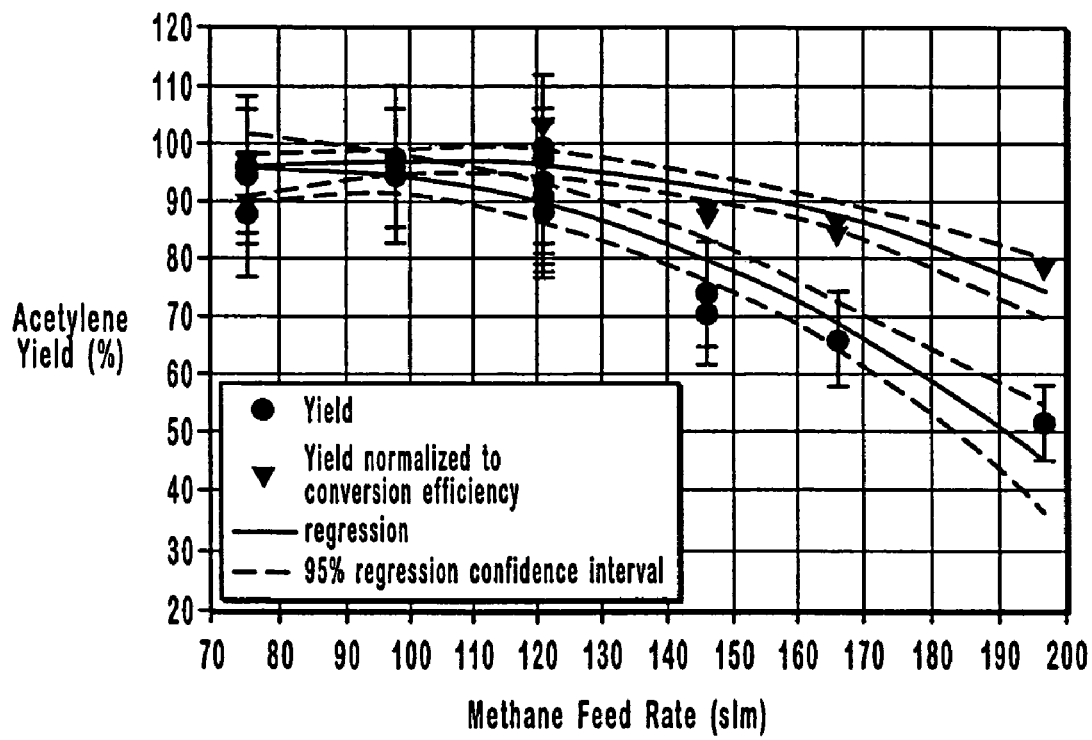
FIG. 9 is a graph plotting acetylene yield as a function of methane injection rate.

Acetylene yield as a function of methane injection rate appears in the graph of FIG. 8. The trends observed in the yield data are similar to those observed in the plot of conversion efficiency, shown in FIG. 5. The acetylene yield was approximately 95% for methane injection rates less than about 100 slm. Further increases in methane injection rate resulted in a decrease of yield. At an injection rate of 145 slm, the theoretical maximum feed rate that can be processed with conversion efficiency and yield approaching 100%, the measured yield dropped to 75%. In FIG. 9, the measured yield has been normalized to account for the measured decrease in conversion efficiency. This normalization is simply:

$$yield_{normalized} = \frac{yield}{conversion efficiency}$$

The normalized yield is a measure of selectivity for conversion to acetylene. As illustrated in the graph of FIG. 9, this normalization accounts for a significant portion of the observed decrease in acetylene yield. Improving the conversion efficiency will flatten the yield curve significantly. This suggests that minimization of the cold boundary layers through improved thermal design can result in an improvement in overall system performance and that the intrinsic acetylene yield is high over a wide range at reactant flow rates (reactor temperature).

Figure 10:
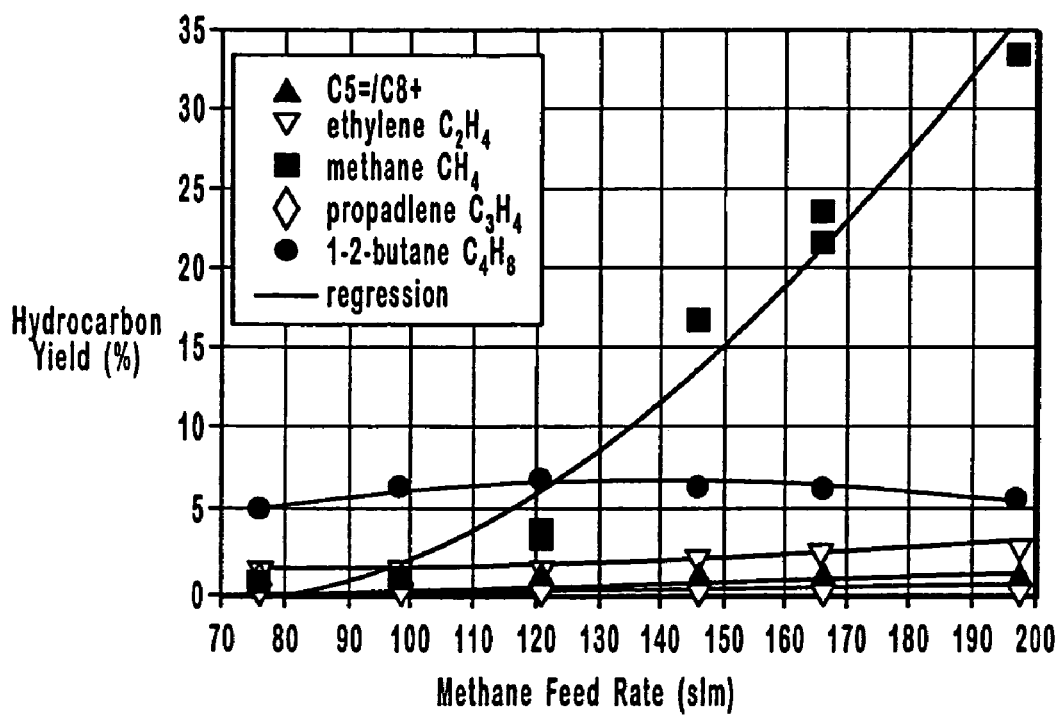
FIG. 10 is a graph plotting hydrocarbon yield as a function of methane injection rate.
Figure 11:
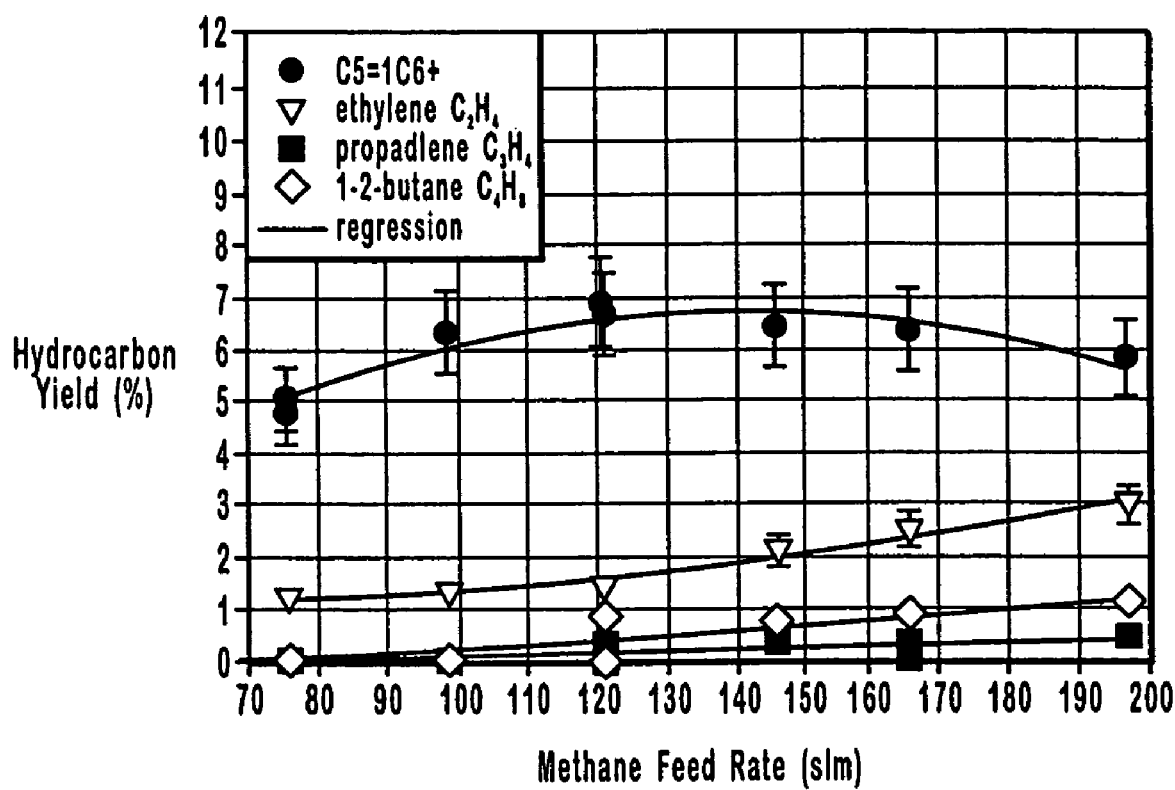
FIG. 11 is a graph plotting hydrocarbon yield, (less methane) as a function of methane injection rate.

The decrease in the measured yield that is not accounted for by the decrease in conversion efficiency is due to the formation of other carbon containing species. These include other hydrocarbons and soot. FIGS. 10 and 11 contain plots of the carbon basis yield of the other hydrocarbon species observed as a function of methane injection rate. Yield is given as a percentage of carbon introduced into the system as methane. The figures are identical except for scale and the absence of methane in FIG. 11. In FIG. 10 the decrease in conversion efficiency with increased methane injection rate is evident in the increase in methane yield. FIG. 11 is the same data plotted on an expanded scale. The observed decrease in the normalized yield is due to an increase in the yield of other carbon containing species. The species represented on the plot are the only ones observed by the gas chromatograph. Interestingly enough, after an initial increase in the yield of olefins plus the $C_6$ and heavier ($C_5=/C_6+$) hydrocarbons the relative amount decreases slightly at higher methane injection rates. These relatively heavy hydrocarbons were subsequently identified as almost entirely benzene by GCMS analysis. The other carbon containing species observed, ethylene, propadiene, and t-2-butene steadily increase as the rate of methane injection increases. The dependence of conversion, yield, and the yield of other hydrocarbon species on the relative amounts of Ar and $H_2$ ratio was examined by decreasing the Ar to $H_2$ ratio by a factor of two. There was no noticeable effect on the conversion efficiency or on the composition of the product stream. Because the product stream is always characterized by an abundance of $H_2$ the Ar present appears to have little or no effect on the kinetics and does not shift the equilibrium of the product stream.

In addition to the tests utilizing methane as the reactant gas, a limited number of runs were performed using pipeline natural gas. The observed conversion efficiencies, acetylene yields and the yields of the other hydrocarbons were identical to the prior results using pure methane as the feedstock. The analyses of the natural gas and product streams appear in Table 2.

Figure 15:
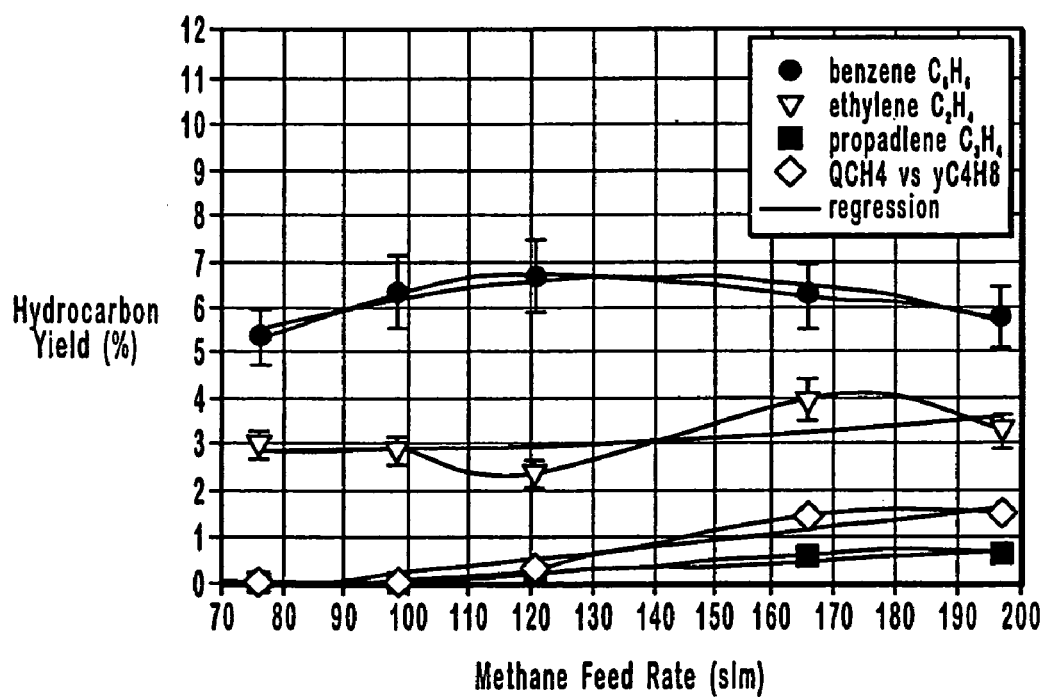
FIG. 15 is a graph plotting hydrocarbon yield, (less methane) as a function of methane feed rate.

The results are virtually identical to the pure methane runs with the exception of the $N_2$, which is essentially inert, and the conversion of the $CO_2$ to CO. In a carbon rich system the $CO$—$CO_2$ equilibrium tends toward CO at relatively modest temperatures on the order of 1000° C.

quench are virtually identical to the earlier results developed with the nozzle present. There appears to be some minor improvement in yield at the higher methane injection rates when the nozzle is present, but the deviations are within the uncertainty estimate and the error bars significantly overlap. Examination of yields of other hydrocarbons, as shown in as shown in FIG. 15, indicate a statistically significant difference in the yields of ethylene between the result with the nozzle removed and with the nozzle in place (FIG. 11).

TABLE 2

Gas Chromatograph analysis of natural gas reactant and product stream in mole percent, 60 kW plasma power, 140 slm Ar, 100 slm $H_2$, and 98.5 slm natural gas

| | $H_2$ | $C5=/C_{6+}$ | Propane $C_3H_8$ | Acetylene $C_2H_2$ | i-Butane $C_4H_{10}$ | n-Butane $C_4H_{10}$ | CO | Ethylene $C_2H_4$ | Ethan $C_2H_6$ | Ar | $N_2$ | Methane $CH_4$ | CO | Solid Carbon Yield |
|---|---|---|---|---|---|---|---|---|---|---|---|---|---|---|
| Natural Gas | 0 | 0.04 | 0.74 | 0 | 0.1 | 0.11 | 0.5 | 0 | 3.79 | 0 | 1.18 | 93.47 | 0 | — |
| Product Stream | 53.5 | 0.34 | 0 | 11.8 | 0 | 0 | 0 | 0.182 | 0 | 33 | 0.44 | 0.21 | 0.2 | 3.2% |

Example 2

In this example the results of experiments without the use of a converging-diverging nozzle are presented. The conversion efficiency (~100% vs. 70%) yield, and selectivity (95% vs. 51%) of the present process demonstrated appear to be somewhat superior to the original Huels process. This may be due to better mixing, temperature uniformity, or more rapid quenching. The Huels product stream analysis as well as the laboratory scale results are summarized in Table 2.

Figure 12:
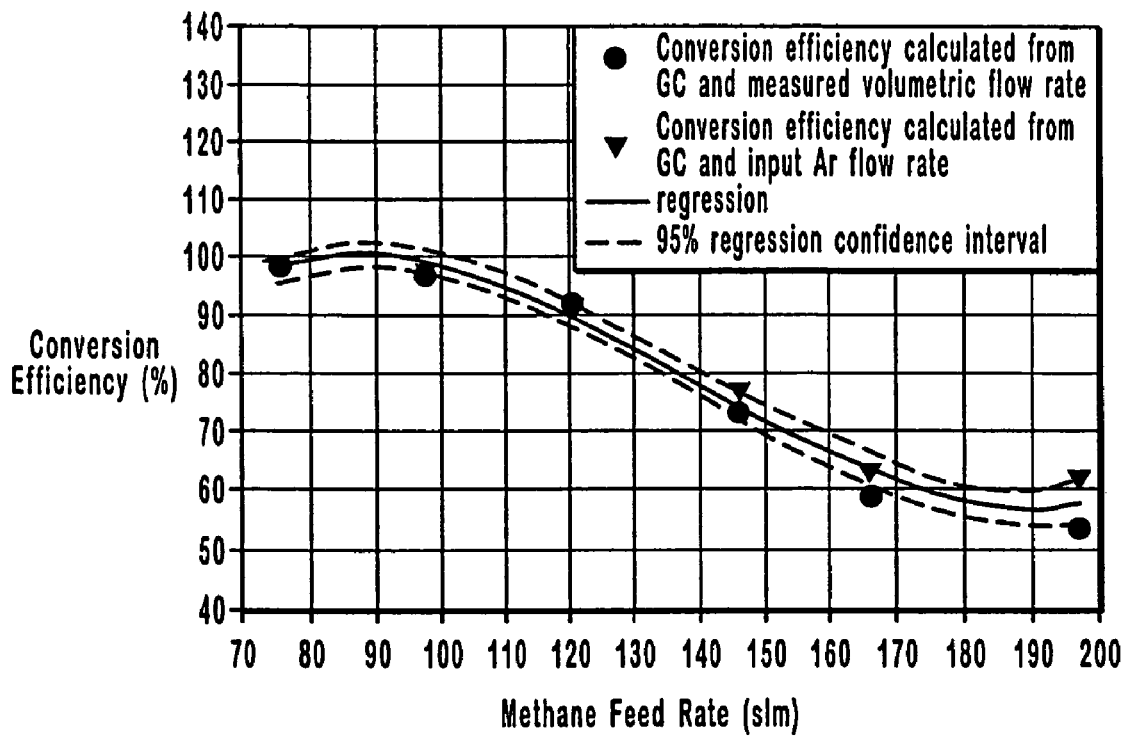
FIG. 12 is a graph plotting conversion efficiency as a function of methane feed rate.
Figure 13:
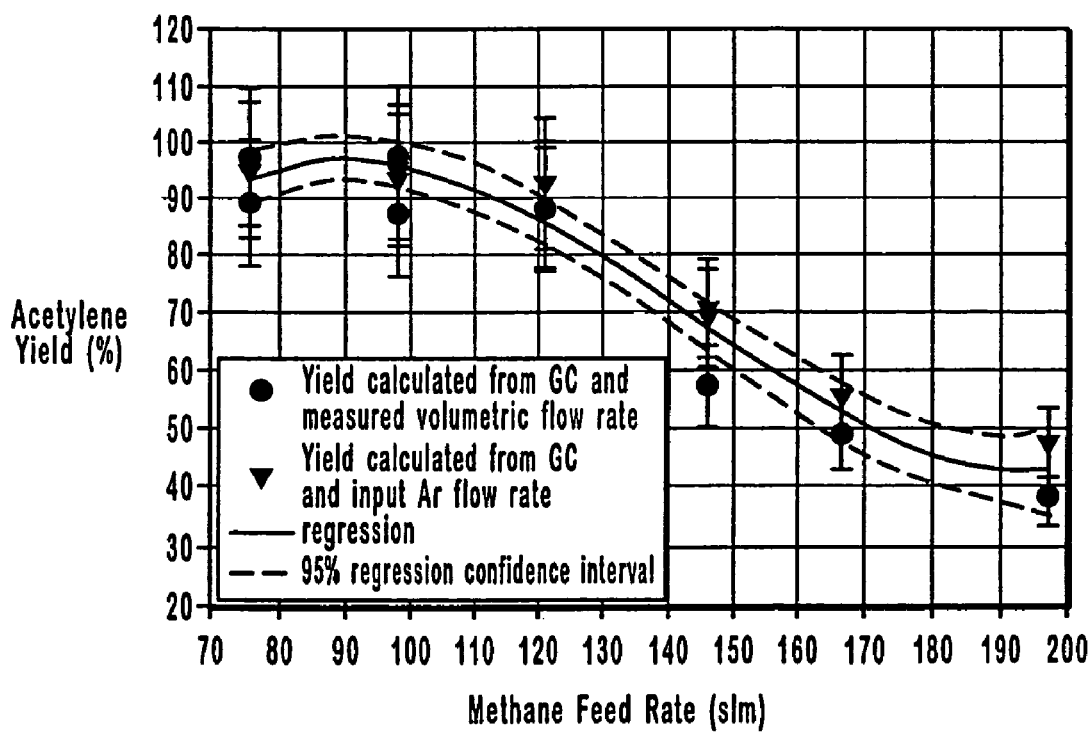
FIG. 13 is a graph plotting acetylene yield as a function of methane feed rate.
Figure 14:
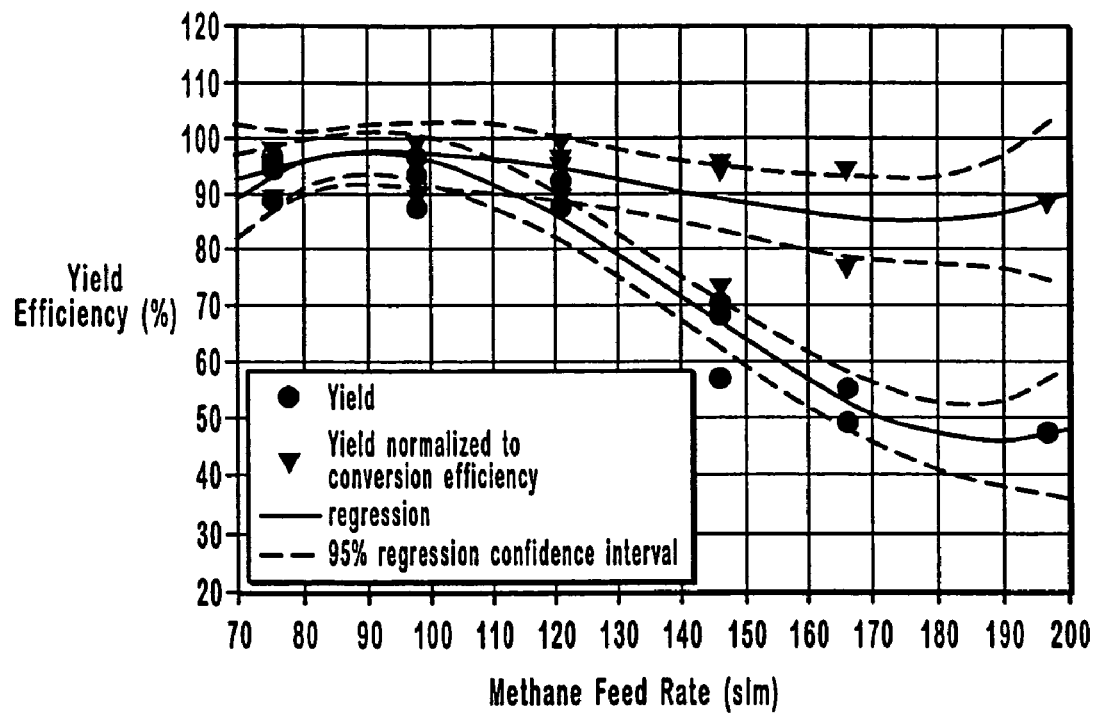
FIG. 14 is a graph plotting yield efficiency as a function of methane feed rate.

To assess the effect of rapid aerodynamic quenching a series of tests, identical to those reported in Example 1 were conducted, but without the converging-diverging nozzle. In these tests the system pressure was maintained at between 700 and 900 torr, approximately the same as the reactor pressure in the test series of Example 1. Conversion efficiency, yield, and normalized yield results are summarized in the graphs of FIGS. 12-14. The yield of other hydrocarbon species is summarized in the graph of FIG. 15.

The yield and conversion efficiency results without the converging-diverging nozzle and supersonic aerodynamic Apparently the high quench rates afforded by the nozzle have the effect of suppressing the formation of ethylene, cutting the yield of ethylene by approximately 30%. The exact mechanism of ethylene formation is as yet undefined; however, it is likely that the kinetics and population of the $CH_2$ radical play an important role.

Figure 16:
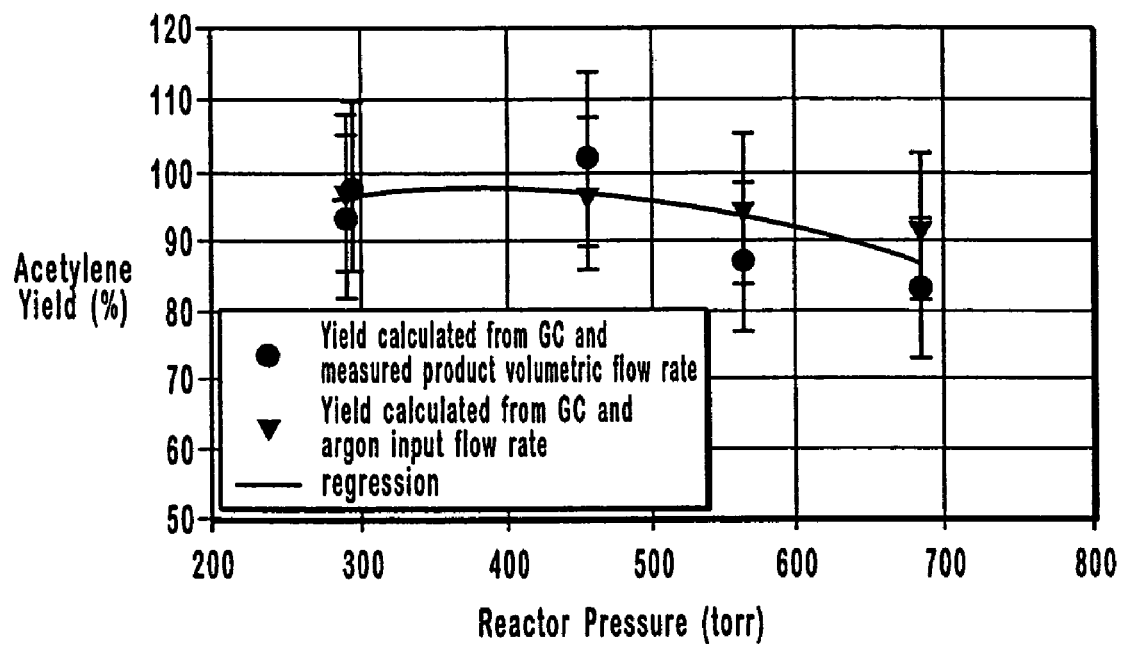
FIG. 16 is a graph plotting acetylene yield as a function of pressure.
Figure 17:
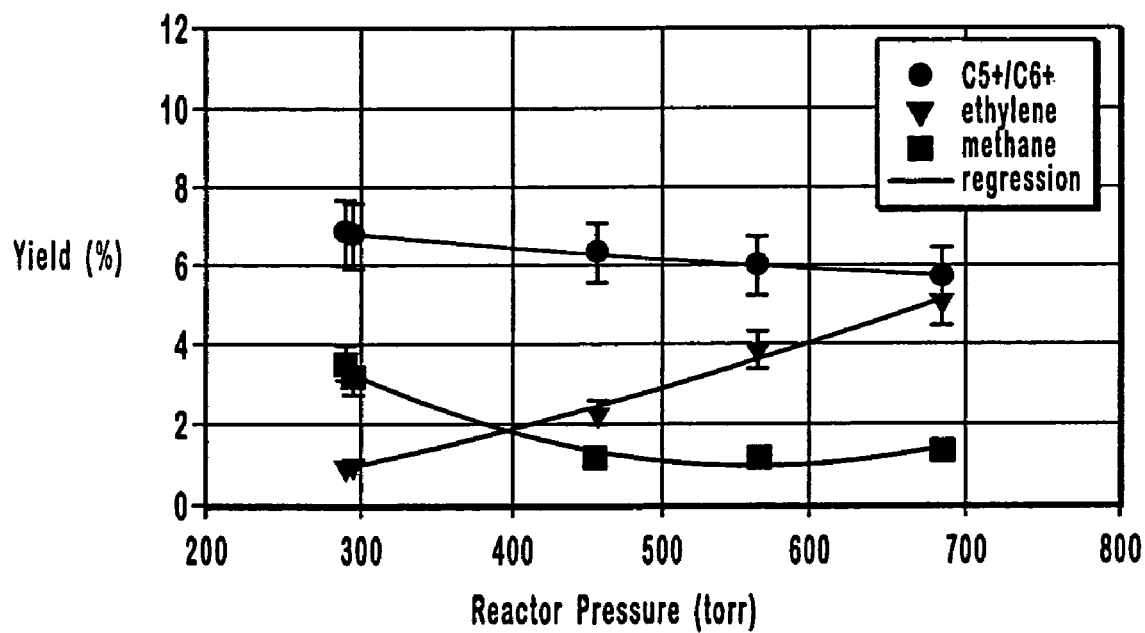
FIG. 17 is a graph plotting hydrocarbon yield as a function of reactor pressure.

With the converging-diverging nozzle removed, the reactor pressure can be independently controlled with a valve. This configuration allows investigation of the effect of pressure on yield. It was demonstrated earlier, as shown in FIG. 7, that pressure and resident time has only a small effect on conversion efficiency. Measured acetylene yield is plotted as a function of reactor pressure in the graph of FIG. 16. The power is constant at 60 kW into the gas and the flow rates are maintained at 160 slm Ar, 100 slm $H_2$, and 98.5 slm $CH_4$. There appears to be a slight decrease in acetylene yield with increasing pressure although the effect is not large. The decrease in yield is accompanied by a slight decrease in benzene yield and an increase in the ethylene yield, as shown in FIG. 17. In general, pressure changes in the range of 300-700 torr do not have a large effect.

TABLE 2

Product stream analysis in mole percent.

| | | Acetylene $C_2H_2$ | Allene $C_3H_4$ | Diacetylene $C_4H_2$ | $C_4H_4$ | Ethylene C2H4 | Methane $CH_4$ |
|---|---|---|---|---|---|---|---|
| Hucls process | feedstock | — | | — | — | — | 92.3 |
| | product | 14.5 | | 0.6 | 0.1 | 0.9 | 16.3 |
| Current process W/quench | feedstock | — | | — | — | — | 93.47 |
| | product* | 11.8 | | — | — | — | 0.21 |

| | | Ethane $C_2H_6$ | Propane $C_3H_8$ | i-Butane $C_4H_{10}$ | n-Butane $C_4H_{10}$ | Benzene $C_6H_6$ | $H_2$ | CO | $N_2$ | Carbon Yield |
|---|---|---|---|---|---|---|---|---|---|---|
| Hucls process | | 1.4 | 0.5 | — | 0.4 | — | — | — | 5.4 | — |
| | | 0.04 | 0.03 | 0.01 | — | 0.3 | 63.4 | 0.6 | 2.7 | 2.7% |
| Current process W/quench | | 3.79 | 0.74 | 0.10 | 0.11 | 0.04 | — | — | 1.18 | — |
| | | — | — | — | — | 0.34 | 53.47 | 0.25 | 0.44 | 3.2% |

*Also includes 33.3 mole percent argon.

Example 3

Comprehensive data for a test run are provided in Tables 3-5 below. The test run was conducted without a converging-diverging nozzle. Table 3 presents a summary of the flow rates, power, measured torch thermal efficiency, nozzle geometry, and reactor and exit pressures.

TABLE 3

| Test SEPT13A-4P | |
|---|---|
| Ar (slm) | 160.4 |
| H2 (slm) | 100.1 |
| CH4 (slm) | 75.9 |
| Net Power (kW) | 60.2 |
| Efficiency % | 85 |
| Geometry | straight |
| Pressure exit (torr) | 409 |
| Pressure reactor (torr) | 550 |

Table 4 presents yield, volume rate, specific energy requirements (SER) and relative yield for the acetylene and hydrogen in the test. The column and row headings are generally sufficient to describe the data contained therein. Specifically, the column labeled Yield %: Qt meas. provides the yield of acetylene and hydrogen from methane feedstock and measured conversion efficiency. The acetylene yield is the percent of the carbon in the methane feedstock that ends up in acetylene and the hydrogen yield is the percent of the hydrogen in the methane feedstock that ends up as elemental hydrogen. Qt denotes measurements based on the downstream turbine flow meter. The column labeled Yield %: Qt At std. provides the yield of acetylene and hydrogen from methane feedstock and measured conversion efficiency. Q Ar std denotes measurements based on input flow rate of argon and gas chromatography data.

The column labeled volume rate (slm) provides the volumetric flow rate of acetylene and hydrogen generated from methane feedstock. Qt denotes measurements based on the downstream turbine flow meter. Q Ar std denotes measurements based on input flow rate of argon and gas chromatography data.

The next four columns provide the specific energy requirements. Qt denotes measurements based on the downstream turbine flow meter. Q Ar std denotes measurements based on input flow rate of argon and gas chromatography data.

The column labeled R yield provides the relative yield. Yield numbers have been normalized for conversion efficiency.

TABLE 4

| | Yield % | | Volume Rate (slm) | | SER Qt meas | SER Q Ar std | SER Qt meas | SER Q Ar std | |
|---|---|---|---|---|---|---|---|---|---|
| | Qt meas | Q Ar std | Qt meas | Q Ar std | kW-hr/kg | kW-hr/kg | kW-hr/Mscf | kW-hr/Mscf | R yield |
| | | | | | | | | | Ar std |
| C2H2 | 98.2 | 96.14 | 37.27 | 36.48 | 23.19 | 23.69 | 765.60 | 782.14 | 0.97 |
| | | | | | | | | | Qt |
| H2 from CH4 | 47.90 | 45.49 | 72.70 | 69.1 | 154.56 | 162.74 | 392.49 | 413.26 | 0.99 |
| Conv. eff % | 99.3 | 99.30 | | | | | | | |

Table 5 presents flow rate and mass balance data for the various species in this test run. The column and row headings are generally sufficient to describe the data contained therein to one skilled in the art. Specifically, the column labeled [conc %] provides the concentration in mole percent measured by gas chromatography. Table 5 is presented in two parts because of its size.

TABLE 5

Part A

| Species | [conc %] | Qin slm | mdot in | Qt meas | mt meas | mdot H in | mdot H out |
|---|---|---|---|---|---|---|---|
| H2 (Hydrogen) | 45.825 | 100.1 | 8.94 | 377.1 | 15.43 | 8.94 | 15.43 |
| C5=/C6 + (C6H6) | 0.217 | 0.0 | 0.00 | 377.1 | 2.85 | 0.00 | 0.22 |
| C3H8 (Propane) | 0.000 | 0.0 | 0.00 | 377.1 | 0.00 | 0.00 | 0.00 |
| C2H2 (Acetylene) | 9.884 | 0.0 | 0.00 | 377.1 | 43.26 | 0.00 | 3.33 |
| C3H6 (Propylene) | 0.000 | 0.0 | 0.00 | 377.1 | 0.00 | 0.00 | 0.00 |
| C4H10 (i-Butane) | 0.000 | 0.0 | 0.00 | 377.1 | 0.00 | 0.00 | 0.00 |
| C3H4 (Propadiene) | 0.000 | 0.0 | 0.00 | 377.1 | 0.00 | 0.00 | 0.00 |
| C4H10 (n-Butane) | 0.000 | 0.0 | 0.00 | 377.1 | 0.00 | 0.00 | 0.00 |
| C4H8 (I-butene) | 0.000 | 0.0 | 0.00 | 377.1 | 0.00 | 0.00 | 0.00 |
| C4H8 (i-Butane/i-Butylene) | 0.000 | 0.0 | 0.00 | 377.1 | 0.00 | 0.00 | 0.00 |

TABLE 5-continued

Part A

| Species | [conc %] | Qin slm | mdot in | Qt meas | mt meas | mdot H in | mdot H out |
|---|---|---|---|---|---|---|---|
| C4H8 (t-2-Butene) | 0.000 | 0.0 | 0.00 | 377.1 | 0.08 | 0.00 | 0.01 |
| C4H8 (c-2-Butene) | 0.008 | 0.0 | 0.00 | 377.1 | 0.00 | 0.00 | 0.00 |
| C4H6 (1.3-Butadiene) | 0.000 | 0.0 | 0.00 | 377.1 | 0.00 | 0.00 | 0.00 |
| C5H12 (i-Pentane) | 0.000 | 0.0 | 0.00 | 377.1 | 0.00 | 0.00 | 0.00 |
| C5H12 (n-Pentane) | 0.000 | 0.0 | 0.00 | 377.1 | 0.00 | 0.00 | 0.00 |
| CO2 (Carbon dioxide) | 0.000 | 0.0 | 0.00 | 377.1 | 0.00 | 0.00 | 0.00 |
| C2H4 (Ethylene) | 0.459 | 0.0 | 0.00 | 377.1 | 2.16 | 0.00 | 0.31 |
| C2H6 (Ethane) | 0.000 | 0.0 | 0.00 | 377.1 | 0.00 | 0.00 | 0.00 |
| Ar (Argon) | 43.454 | 160.4 | 286.43 | 377.1 | 292.62 | 0.00 | 0.00 |
| N2 (Nitrogen) | 0.000 | 0.0 | 0.00 | 377.1 | 0.00 | 0.00 | 0.00 |
| CH4 (Methane) | 0.145 | 75.9 | 54.21 | 377.1 | 0.39 | 13.55 | 0.10 |
| CO (Carbon monoxide) | 0.000 | 0.0 | 0.00 | 377.1 | 0.00 | 0.00 | 0.00 |
| TOTAL g/min | | | 349.58 | | 356.79 | 22.49 | 19.39 |
| % difference | | | | | −2.06 | | 13.77 |
| % Soot produced based on carbon balance | | | | | | | |

TABLE 5

Part B

| Species | mdot C in | mdot C out | yield Qt | Q Ar std | mt Ar std | mdot H Ar | mdot C Ar std | yield Ar std |
|---|---|---|---|---|---|---|---|---|
| H2 (Hydrogen) | 0.00 | 0.00 | 0.0 | 369.13 | 15.10 | 15.10 | 0.00 | 0.0 |
| C5═/C6 + (C6H6) | 0.00 | 2.63 | 6.5 | 369.13 | 2.79 | 0.21 | 2.58 | 6.34 |
| C3H8 (Propane) | 0.00 | 0.00 | 0.0 | 369.13 | 0.00 | 0.00 | 0.00 | 0.00 |
| C2H2 (Acetylene) | 0.00 | 39.93 | 98.2 | 369.13 | 42.35 | 3.26 | 39.09 | 96.14 |
| C3H6 (Propylene) | 0.00 | 0.00 | 0.0 | 369.13 | 0.00 | 0.00 | 0.00 | 0.00 |
| C4H10 (i-Butane) | 0.00 | 0.00 | 0.0 | 369.13 | 0.00 | 0.00 | 0.00 | 0.00 |
| C3H4 (Propadiene) | 0.00 | 0.00 | 0.0 | 369.13 | 0.00 | 0.00 | 0.00 | 0.00 |
| C4H10 (n-Butane) | 0.00 | 0.00 | 0.0 | 369.13 | 0.00 | 0.00 | 0.00 | 0.00 |
| C4H8 (I-butene) | 0.00 | 0.00 | 0.0 | 369.13 | 0.00 | 0.00 | 0.00 | 0.00 |
| C4H8 (i-Butane/i-Butylene) | 0.00 | 0.00 | 0.0 | 369.13 | 0.00 | 0.00 | 0.00 | 0.00 |
| C4H8 (t-2-Butene) | 0.00 | 0.07 | 0.2 | 369.13 | 0.08 | 0.01 | 0.07 | 0.16 |
| C4H8 (c-2-Butene) | 0.00 | 0.00 | 0.0 | 369.13 | 0.00 | 0.00 | 0.00 | 0.00 |
| C4H6 (1.3-Butadiene) | 0.00 | 0.00 | 0.0 | 369.13 | 0.00 | 0.00 | 0.00 | 0.00 |
| C5H12 (i-Pentane) | 0.00 | 0.00 | 0.0 | 369.13 | 0.00 | 0.00 | 0.00 | 0.00 |
| C5H12 (n-Pentane) | 0.00 | 0.00 | 0.0 | 369.13 | 0.00 | 0.00 | 0.00 | 0.00 |
| CO2 (Carbon dioxide) | 0.00 | 0.00 | 0.0 | 369.13 | 0.00 | 0.00 | 0.00 | 0.00 |
| C2H4 (Ethylene) | 0.00 | 1.85 | 4.6 | 369.13 | 2.12 | 0.30 | 1.82 | 4.47 |
| C2H6 (Ethane) | 0.00 | 0.00 | 0.0 | 369.13 | 0.00 | 0.00 | 0.00 | 0.00 |
| Ar (Argon) | 0.00 | 0.00 | 0.0 | 369.13 | 286.43 | 0.00 | 0.00 | 0.00 |
| N2 (Nitrogen) | 0.00 | 0.00 | 0.0 | 369.13 | 0.00 | 0.00 | 0.00 | 0.00 |
| CH4 (Methane) | 40.66 | 0.29 | 0.7 | 369.13 | 0.38 | 0.10 | 0.29 | 0.70 |
| CO (Carbon monoxide) | 0.00 | 0.00 | 0.0 | 369.13 | 0.00 | 0.00 | 0.00 | 0.00 |
| TOTAL g/min | 40.66 | 44.78 | 110.1 | | 349.25 | 18.98 | 43.84 | 107.8 |
| % difference | | −10.14 | | | 0.09 | 15.59 | −7.81 | |
| % Soot produced based on carbon balance. | | −10.14 | | | | | −7.81 | |

The measured conversion efficiency and acetylene yield in the laboratory reactor system described here in Examples 1 and 2 are in general somewhat better than reported in the literature; conversion efficiencies (CE) approach 100% and yields in the 90-95% range with 2-4% soot produced have been demonstrated. This appears to be somewhat of an improvement over the Huels process (CE=70.5% and yC$_2$H$_2$=51.4%, 2.7% carbon soot) and the DuPont process (CE-not reported, yC$_2$H$_2$=70%). The process reported here also appears to have somewhat better specificity for acetylene. The improvement in conversion efficiency, yield and specificity are due primarily to improved injector design and mixing (a better "stirred" reactor) and minimization of temperature gradients-and cold boundary layers. The rate of cooling by wall heat transfer appears to be sufficient to quench the product stream and prevent further decomposition of acetylene into soot or further reaction leading to heavier hydrocarbon products. Significantly increasing the quench rate by rapidly expanding the product stream through a converging-diverging nozzle leads to only marginal improvement in the composition of the product stream, primarily the reduction of the yield of ethylene.

Figure 18:
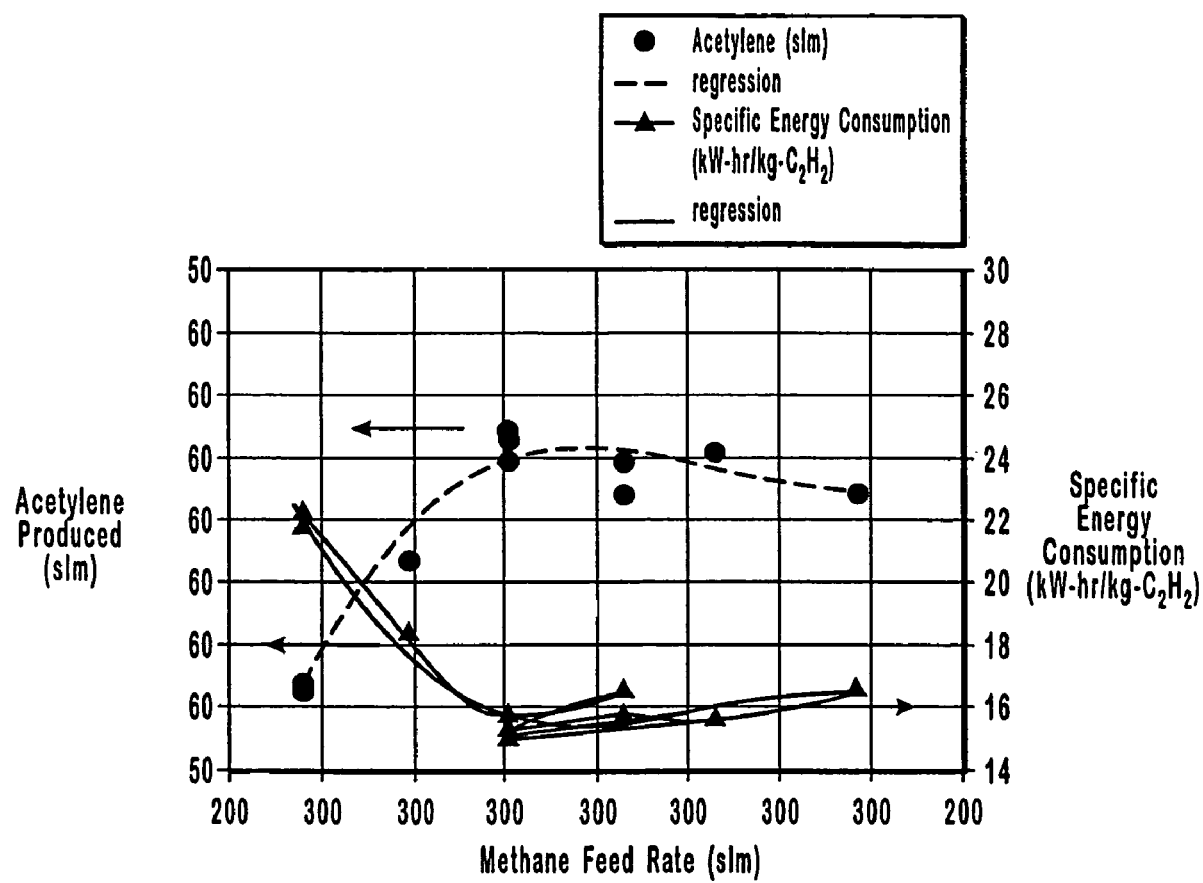
FIG. 18 is a graph plotting acetylene produced and specific energy consumption as a function of methane feed rate.

The specific amount of energy consumed (kW-hr) per amount (kg) of acetylene produced ultimately determines the economics of the process. The Huels process reportedly consumed 12.1 kW-hr/kg-$C_2H_2$ produced. The DuPont process specific energy consumption was estimated, though not measured, to be 8.8 kW-hr/kg-$C_2H_2$ produced. This later value compares favorably with the theoretical minimum value of approximately 7.9 kW-hr/kg-$C_2H_2$ for a product stream at 2000° C., 100% conversion efficiency and yield and no electrical or thermal losses. The measured specific energy consumption for the laboratory scale process examined in this study is plotted in the graph of FIG. 18. The minimum measured specific energy consumption is approximately 16 kW-hr/kg-$C_2H_2$ produced. It is estimated that this could be improved to a value of around 13 kW-hr/kg-$C_2H_2$ by improved thermal design. This includes moving the injection into the torch body thus avoiding the thermal losses in the injector ring and reducing the thermal losses in the reactor section. Process heat recovery might further reduce the specific energy consumption by another 20% or so to around the 10 kW-hr/kg-$C_2H_2$ range. These numbers compare favorably with the specific energy consumption reported for the Huels and DuPont processes while demonstrating improved conversion efficiency and yield.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for thermal conversion of one or more reactants to at least one desired end product, the apparatus comprising:
    an axial reactor having an inlet end, an outlet end, a reaction zone between the inlet end and the outlet end, and a reactor inlet at the inlet end;
    a torch section configured to produce a heating gas; and
    an injector section interposed between the torch section and the axial reactor, the injector section including a heating gas inlet and at least one reactant inlet, the heating gas inlet and the at least one reactant inlet configured to provide all of the one or more reactants at a restricted diameter injection line within the injector section, the injector section being sized, located and configured to introduce one or more reactants into the heating gas and to promote substantially thorough mixing of the one or more reactants with the heating gas to produce a stream flowing axially toward the reactor inlet of the axial reactor, wherein the torch section, the injector section and the axial reactor are cooperatively configured such that any gas passing through the axial reactor enters the axial reactor through the inlet of the axial reactor.

2. The apparatus of claim 1, further comprising a convergent-divergent nozzle located coaxially with, and at an intended downstream location of, the outlet end of the axial reactor for rapidly cooling the gaseous stream by converting thermal energy to kinetic energy as a result of adiabatic and isentropic expansion as the stream flows axially through the nozzle.

3. The apparatus of claim 2, wherein the convergent-divergent nozzle has a converging section and a diverging section respectively leading to and from a restrictive open throat, the diverging section having a conical configuration centered along an axis of the axial reactor.

4. The apparatus of claim 2, further comprising a cooling section leading from the convergent-divergent nozzle.

5. The apparatus of claim 4, wherein the cooling section is configured to reduce the velocity of the stream while removing heat energy at a rate sufficient to prevent increases in its kinetic temperature and to retain the at least one desired end product within the stream.

6. The apparatus of claim 1, further comprising a cooling section in fluid communication with the outlet end of the axial reactor.

7. The apparatus of claim 6, wherein the cooling section is configured to reduce the velocity of the stream while removing heat energy at a rate sufficient to prevent increases in its kinetic temperature and to retain the desired end product within the stream.

8. The apparatus of claim 6, further comprising a converging section that connects the outlet end of the axial reactor to the cooling section.

9. The apparatus of claim 1, wherein the injector section comprises a multi-port injector located in an injector line.

10. The apparatus of claim 1, wherein the torch section includes an anode injector.

11. The apparatus of claim 1, further comprising an insulating layer surrounding the reaction zone.

12. The apparatus of claim 1, wherein the torch section comprises a plasma torch having a plasma arc inlet for introducing a stream of plasma arc gas to the plasma torch to produce a plasma.

13. The apparatus of claim 12, wherein the plasma torch includes at least one pair of electrodes positioned at an intended upstream location relative to the inlet end of the reactor.

14. The apparatus of claim 1, wherein the injector section comprises an injection line having a smaller diameter than a diameter of the reaction zone.

15. The apparatus of claim 11, wherein the insulating layer comprises a material selected from the group consisting of carbon, boron nitride, zirconia, silicon carbide, and combinations thereof.

16. The apparatus of claim 15, further comprising a cooling layer surrounding the insulating layer.

17. The apparatus of claim 1, further comprising a cooling section adjacent at least a portion of the reaction zone.

18. The apparatus of claim 17, wherein the cooling section is configured to circulate a liquid adjacent the at least a portion of the reaction zone.

* * * * *

UNITED STATES PATENT AND TRADEMARK OFFICE
CERTIFICATE OF CORRECTION

PATENT NO. : 7,576,296 B2  Page 1 of 1
APPLICATION NO. : 10/843965
DATED : August 18, 2009
INVENTOR(S) : Fincke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1297 days.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

Page 1 of 2

PATENT NO. : 7,576,296 B2
APPLICATION NO. : 10/843965
DATED : August 18, 2009
INVENTOR(S) : James R. Fincke et al.

It is certified that error appears in the above-identified patent and that said Letters Patent is hereby corrected as shown below:

On the title page:
In ITEM (56) References Cited
U.S. PATENT DOCUMENTS
    Page 2, 1st column, Line 16      change "Mogensen etal." to --Mogensen et al.--

OTHER PUBLICATIONS
    Page 2, 2nd column, 1st line of the
    3rd entry, (line 62)      change "Mettalurgy"." to --Metallurgy."--

In the specification:
| | | |
|---|---|---|
| COLUMN 1, | LINE 3, | change "RELATED APPLICATION" to --CROSS-REFERENCE TO RELATED APPLICATIONS-- |
| COLUMN 1, | LINE 25, | change "DE-AC07-99ID 13727" to --DE-AC07-99ID13727-- |
| COLUMN 1, | LINE 41, | change "State." to --States.-- |
| COLUMN 9, | LINE 27, | change "reactants is preferably" to --reactants preferably-- |
| COLUMN 9, | LINE 47, | change "on embodiment" to --one embodiment-- |
| COLUMN 10, | LINE 37, | change "throat" to --throat 26-- |
| COLUMN 11, | LINE 9, | change "change" to --changes-- |
| COLUMN 11, | LINE 15, | change "throat." to --throat 26.-- |
| COLUMN 11, | LINE 37, | change "throat." to --throat 26.-- |
| COLUMN 11, | LINE 44, | change "throat" to --throat 26-- |
| COLUMN 11, | LINE 45, | change "section of the nozzle" to --section 28 of the nozzle 18-- |

Signed and Sealed this
Twenty-ninth Day of May, 2012

David J. Kappos
*Director of the United States Patent and Trademark Office*

CERTIFICATE OF CORRECTION (continued)
U.S. Pat. No. 7,576,296 B2

In the specification (continued):

| | | |
|---|---|---|
| | COLUMN 12, LINES 5,6 | change "diverging section" to --diverging section 28-- |
| | COLUMN 12, LINE 62, | change "turbulant" to --turbulent-- |
| | COLUMN 15, LINE 17, | change "greater that" to --greater than-- |
| COLUMN 18, TABLE 2 (upper), | | |
| 9th column heading | | change "Ethan" to --Ethane-- |
| COLUMN 18, TABLE 2 (lower), | | |
| 1st row heading | | change "Hucls" to --Huels-- |
| COLUMN 18, TABLE 2 (lower) | | |
| 6th row heading | | change "Hucls" to --Huels-- |
| | COLUMN 20, LINE 7, | change "Qt At" to --Qt Ar-- |
| | COLUMN 22, LINE 65, | change "gradients-and" to --gradients and-- |
| | COLUMN 23, LINE 12, | change "This later" to --This latter-- |